United States Patent
Ross et al.

(10) Patent No.: US 6,207,411 B1
(45) Date of Patent: Mar. 27, 2001

(54) BACTERIOCINS

(75) Inventors: Reynolds Paul Ross, Kilworth; Mary Clare Rea, Fermoy; Marie Philippa Ryan, Freighduff; Colin Hill, Friars Wk., all of (IE)

(73) Assignee: Teagasc, Dublin (IE)

( * ) Notice: Subject to any disclaimer, the term of this patent is extended or adjusted under 35 U.S.C. 154(b) by 0 days.

(21) Appl. No.: 08/945,081

(22) PCT Filed: Apr. 12, 1996

(86) PCT No.: PCT/IE96/00022

§ 371 Date: Apr. 13, 1998

§ 102(e) Date: Apr. 13, 1998

(87) PCT Pub. No.: WO96/32482

PCT Pub. Date: Oct. 17, 1996

(30) Foreign Application Priority Data

Apr. 12, 1995 (IE) .................................. S950269

(51) Int. Cl.⁷ .................................. C12N 15/00
(52) U.S. Cl. .................. 435/69.1; 435/252.9; 435/320.1; 435/252.3; 435/172.1; 514/12; 530/324; 530/326; 530/325; 536/23.7
(58) Field of Search .............................. 514/12; 530/324, 530/325, 326; 435/252.9, 320.1, 252.3, 69.1, 172.1; 536/23.7

(56) References Cited

FOREIGN PATENT DOCUMENTS 0 573 763 A3   4/1993   (EP) .

OTHER PUBLICATIONS

Dufour, A. et al. "Plasmid–encoded determinants for bacteriocin production and immunity in a *Lactococcus lactis* strain and purification of the inhibitory peptide." Journal of General Microbiology (Oct. 1991), vol. 137, No. 10, pp. 2423–2429.*

Piard, J.C. et al. "Structure, Organization, and Expression of the lct Gene for Lacticin 481, a Novel Lantibiotic Produced by *Lactococcus lactis*" *J. Bio. Chem.* 268(22):16361–8 (1993).

Ryan, M.P. et al. "An Application in Cheddar Cheese Manufacture for a Strain of *Lactococcus lactis* Producing a Novel Broad–Spectrum Bacteriocin, Lacticin 3147" *Applied and Environ. Microbiol.* 62(2):612–19 (1996).

* cited by examiner

Primary Examiner—Bradley Sisson
Assistant Examiner—Enrique D. Longton
(74) Attorney, Agent, or Firm—Morrison & Foerster LLP

(57) ABSTRACT

The present invention relates to a novel anti-microbial agent, more particularly, a novel bacteriocin with nisin-like properties. The bacteriocin is designated lacticin 3147 and has the following properties: a molecular weight of approximately 2.8 kDa; inhibiting activity against lactococci, lactobacilli, enterococci, bacilli, leuconostocs, pediococci, clostridia, staphylococci and streptococci; sensitivity to the proteases trypsin, alpha-chymotrypsin, proteinase K and pronase E but not pepsin; heat-stability; activity at acid pH; and the capability of inhibiting nisin-producing bacterial strains.

36 Claims, 9 Drawing Sheets

Figure 3:
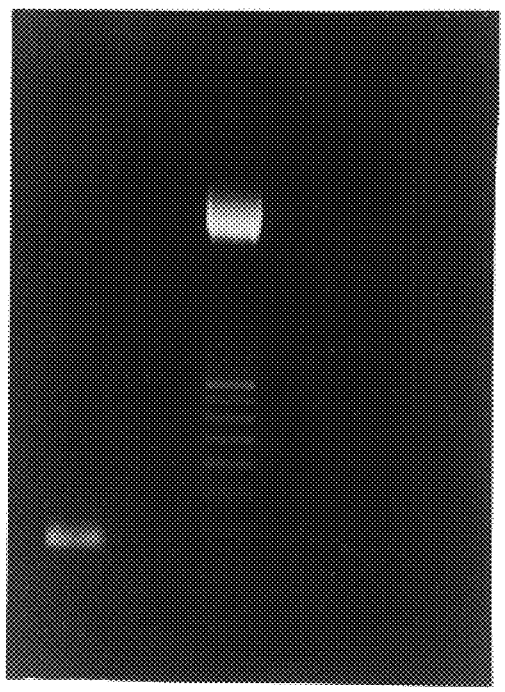

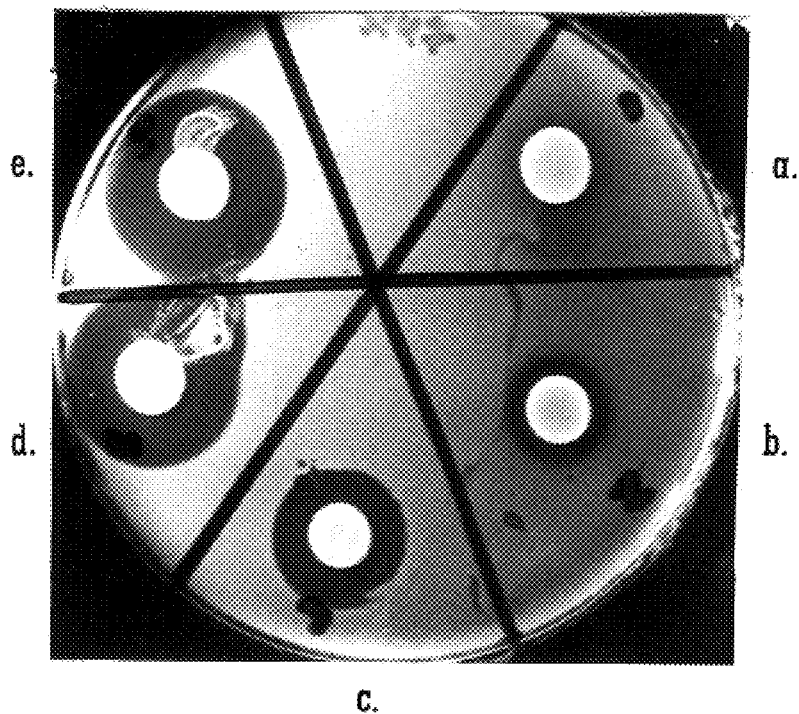
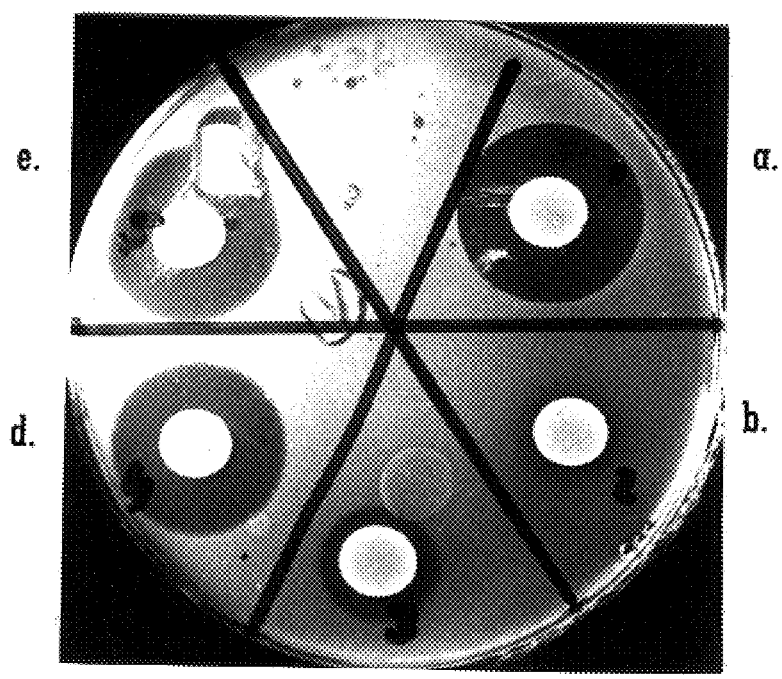
FIG. 1

A
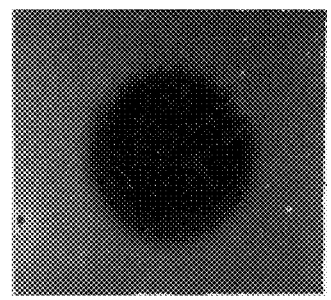
B
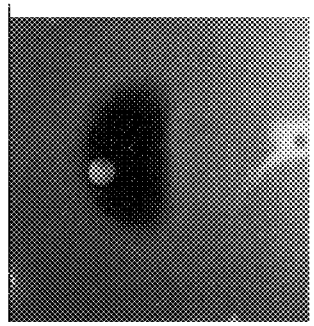
C
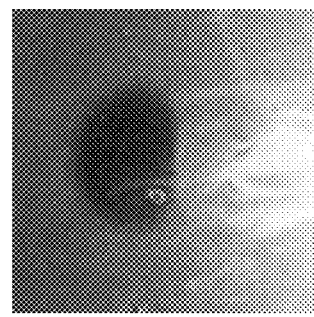
D
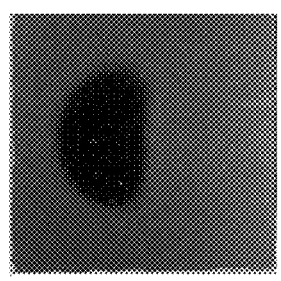
E
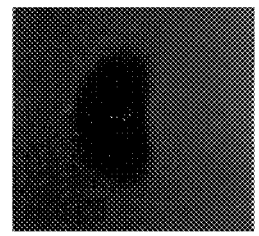
FIG. 2

Growth of L. lactis DPC3147 in GM17 (--○--) and TYT30 (—△—). Production of lacticin 3147 is indicated as follows; ▨, GM17; ▩, TYT30.

Effect of heating at 60 °C to 121 °C for 10 minutes on the stability of lacticin 3147 at pH 5 (—□—), pH 7 (—◇—), pH 9 (--○--). 100% activity is that activity at pH 5, 7 and 9 with no heating.

pH profiles during cheddar cheese manufacture. Control (□); Kefir isolates (●).

Growth of starter (open symbols) and NSLAB (closed symbols) during ripening of cheddar cheese. Control (□, ■); Kefir isolates (○, ●).

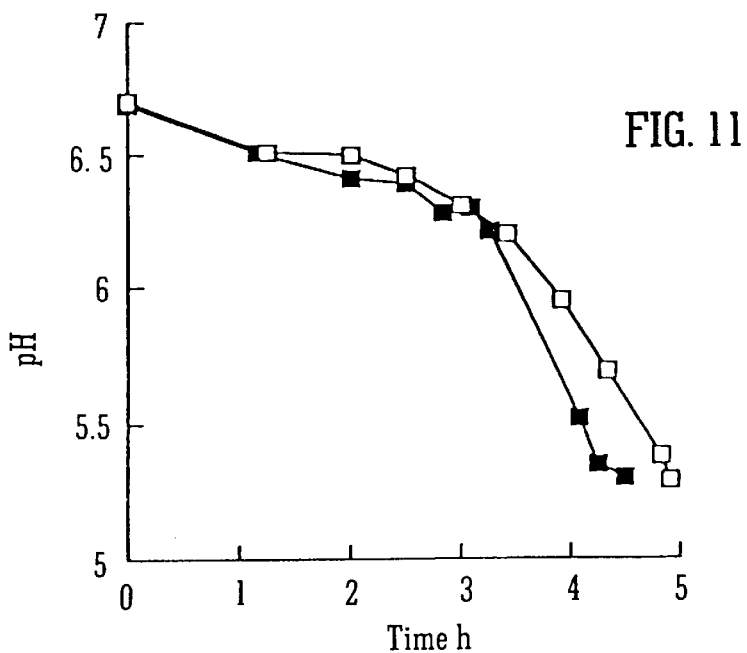
pH profiles during cheese manufacture.
Control 303 (-□-); 303( pMRC 01) (-■-).
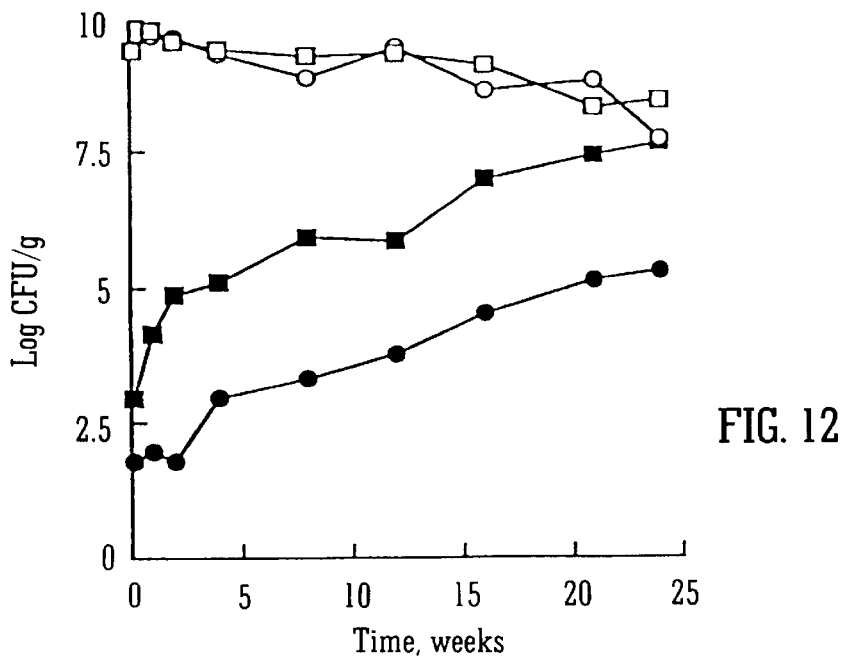
Growth of starter (open symbols) and NSLAB (closed symbols) during ripening. Control 303 (-□- -■-); 303(pMRC 01) (-○- -●-).

BACTERIOCINS

This application claims priority to PCT/IE96/00022, filed Apr. 12, 1996 and Irish patent application S950269, filed Apr. 12, 1995.

The present invention relates to a novel anti-microbial agent, more particularly, a novel bacteriocin with nisin-like properties.

Recent years have seen major advances in the development of microbial metabolites with antagonistic activities towards spoilage and pathogenic micro-organisms associated with food. Although, there now exists in excess of seven thousand known antibiotic compounds of microbial origin, very few have been evaluated for food use. The danger exists that antibiotic-resistant microorganisms of clinical importance will appear with repeated exposure to antibiotics in food, thus compromising the clinical usefulness of the antibiotics (although, of course, clinically important antibiotics are not used for food applications). Additionally, consumer emphasis is now on minimally processed foods which are natural and preservative free. Because of this considerable and justifiable resistance to the use of chemical additives and antibiotics as food preservatives, other biological inhibitors produced by microorganisms are currently being investigated for use in foods. Of particular interest are those inhibitory substances produced by the Lactic Acid Bacteria (LAB) which include hydrogen peroxide, diacetyl, bacteriocins, as well as secondary reaction products such as hypothiocyanite. Bacteriocins are potentially very attractive natural preservatives as they are produced as normal by-products of microbial metabolism. The LAB are industrially important microorganisms and include the genera Lactococcus, Streptococcus, Pediococcus, Leuconostoc, Lactobacillus and Carnobacterium. They have been used for the production of fermented foods which have been consumed safely for hundreds of years. Given their status as "safe" organisms, they are a particularly suitable source for natural antimicrobials such as bacteriocins for use in foods.

In 1925, the first prototype bacteriocin was discovered by Gratia et. al. from a strain of *Escherchia coli*. Bacteriocins are always proteins which can be broad or narrow spectrum and are not lethal to the cells which produce them. Bacteria protect themselves from the lethal effects of their own bacteriocins by such mechanisms as post-translational modification or the production of an immunity protein(s). In any case, bacteriocins are potent antibacterial substances produced by a large and diverse assortment of species. They form a heterogeneous group with respect to their producer, inhibitory spectrum, mode of action and chemical properties. There are four distinct classes of LAB bacteriocins:

A. Lantibiotics—small peptides of less than 5 kDa which contain unusual amino acids such as lanthionine, β-methyllanthionine and dehydrated residue, e.g. nisin, lacticin 481, carnocin U149 and lactocin S.

B. Non-Lanthionine containing Peptides—small peptides of 10 kDa or less and can be subdivided as follows: (i) Listeria-active peptides e.g. Pediocin PA-1 and Sakacin A. (ii) Poration complexes consisting of two proteinaceous peptides e.g. Lactacin F. (iii) Thiol-activated peptides requiring reduced cysteine residues for activity e.g. Lactococcin B.

C. Large Heat-Labile Proteins—larger proteins, generally having a molecular weight greater than 31 kDa e.g. Helveticin V-1829.

D. Complex Bacteriocins—composed of a protein with one or more chemical moieties which may be of a lipid or carbohydrate nature e.g. Pediocin SJ-1.

Lactococci are widely used as starter cultures in the dairy industry and several strains of dairy species can produce bacteriocins. *L. lactis* subspecies can produce diplococcin, lactococcin, lactostrepcins or nisin. Diplococcin and lactococcins are small molecular weight proteins, active against other lactococci while nisin is a lantibiotic with a broad spectrum of activity against many Gram positive bacteria.

Nisin is the most extensively characterised bacteriocin of the antimicrobial proteins produced by LAB and has found widespread application in the food industry. Nisin was the first "antibiotic" compound to be used on a commercial scale in the food industry. It is used to prevent spore outgrowth and toxin production by *Clostridium botulinum* in processed cheese and cheese spreads. In some countries, it has been used to extend the shelf-life of dairy products and to prevent the spoilage of canned foods by thermophiles.

Nisin is a pentacyclic, subtype A lantibiotic and it displays an amphiphathic character, with a hydrophobic residue (Ile) at its N-terminus and a hydrophilic residue (Lys) at its C-terminus. It is a peptide of 34 amino acids and is inactivated by proteases including chymotrypsin, pancreatin and subtilopeptidase. It is insensitive to carboxypeptidase A, elastase, erepsin, pepsin and trypsin. It contains one lanthionine residue, four β-methyllanthionines, a dehydroalanine and a dehydrobutyrine. The thioether amino acids, (lanthionine and β-methyllanthionine) account for the high sulphur content of nisin. The usual amino acid residues are thought to be responsible for the important functional properties of nisin e.g. the associated acid tolerance and thermostable properties of nisin are attributed to the stable thioether linkages while the specific bactericidal activity is thought to be due to the very reactive double bonds. Nisin has a molecular mass of 3.5 kDa (Gross & Morell, 1971) and often forms dimers and oligomers.

Nisin has a very broad spectrum of activity against Gram positive vegetative bacterial cells. The closely related lactococci are especially sensitive but nisin is also inhibitory to several strains of bacilli and clostridia (particularly their spores), lactobacilli, leuconostocs, micrococci, pediococci, streptococci and actinonycetes. Other sensitive strains include *Mycobacterium tuberculosis, Staphylococcus pyogenes, S. aureus, S. epidermidis* and *Listeria monocytogenes* (de Vuyst & Vandamme, 1994). Nisin does not display activity against Gram negative bacteria, except for three Neisseria strains (Mattick & Hirsch, 1947) and three Flavobacter strains (Ogden & Tubb, 1985), nor does it inhibit yeasts or viruses. However, Salmonella subspecies and other Gram negative bacteria can be made sensitive by using a chelating agent in combination with nisin (Stevens et. al. 1992). The site of action of nisin appears to be the cytoplasmic membrane. The outer membrane of Gram negative bacteria is thought to exclude the bacteriocin making contact with the cytoplasmic membrane. Hence, by incorporating a chelating agent such as EDTA with nisin, the structure of the outer membrane undergoes alteration, resulting in destabilization of the lipopolysaccharide (LPS) layer with a corresponding increase in cell permeability. Binding of the bacteriocin to the membrane leads to the aggregation of similar peptides, thus initiating oligomerization. Such aggregates adopt a transmembrane orientation so that the hydrophobic portion is exposed to the core of the membrane and the hydrophilic part forms the aqueous channel. Membrane insertion, pore formation, (both of which require a transmembrane potential) and subsequent depolarization leads to the efflux of small cellular constituents and destruction of energy metabolism of the cell (Ruhr & Sahl, 1985). This results in a deficiency of metabolic intermediates and hence, inhibition of synthesis of DNA, RNA, proteins and polysaccharides. There appears to be a separate mechanism for the prevention of spore outgrowth. Unlike vegetative cells, bacterial spores never lyse when treated with nisin. The dehydro residues of nisin provide possible covalent attachment sites for membrane sulfhydryl groups. These residues appear to have no such role in membrane pore formation (Morris et. al. 1984).

Nisin is encoded by a conjugative transposon which can insert into either plasmid DNA or chromosomal DNA (Horn et. al., 1991). Analysis of the nisin operon indicates that the nisin structural gene, as well as the genes required for processing and maturation are clustered over a polycistronic region exceeding 8.5 kb (Steen et. al., 1991).

Nisin has certain disadvantages for industrial application, one being that resistance to the bacteriocin can frequently occur. For example there is a nisin resistance gene (as opposed to an immunity gene) on the conjugative lactococcal plasmid pNP40. Its second disadvantage is that nisin-producing strains are generally not good acid producers, are phage sensitive and are non-proteolytic and therefore are not efficient cheese starter cultures.

It is an object of the present invention to provide a bacteriocin suitable for food use, particularly one which has a broad spectrum of inhibition and for which there is no detectable spontaneous resistance thereto. A further object is to provide bacteriocin encoding gene(s) which may be more easily conjugally mobilized that the nisin-encoding gene.

It is also an object to provide bacteriocin encoding gene(s) which may be easily conjugally mobilised along with genes which may be attached to them. It is a further object to provide bacteriocin-encoding gene(s) which are not linked to lactose catabolism genes. There is a further object to provide bacteriocin-producing strains which are effective cheese starters. A further object of the invention is to provide phage resistance genes, particularly such genes linked to bacteriocin-encoding genes.

According to the present invention there is provided a bacteriocin characterised by a molecular weight of approximately 2.8 kDa, inhibiting activity against lactococci, lactobacilli, enterococci, bacilli, leuconostocs, pediococci, clostridia, staphylococci and streptococci, sensitivity to the proteases trypsin, alpha-chymotrypsin, proteinase K and pronase E but not pepsin, heat-stability, activity at acid pH, and the capability of inhibiting nisin-producing bacterial strains.

The bacteriocin is designated lacticin 3147. The bacteriocin lacticin 3147-encoding gene does not cross-hybridise with the nisin-encoding gene.

The invention also relates to *L. lactis* DPC3147 strain as deposited at the National Collection of Industrial and Marine Bacteria, Aberdeen, Scotland, on Apr. 11, 1995 under the Accession No. NCIMB 40716. This strain produces the bacteriocin lacticin 3147.

The present invention also provides a 63 kDa plasmid encoding the bacteriocin as defined above. The plasmid may be the plasmid pMRC01 which encodes the novel bacteriocin designated lacticin 3147 and lacticin 3147 immunity genes, as deposited in the National Collection of Industrial and Marine Bacteria, Aberdeen, Scotland on Apr. 11, 1995 under the Accession Number NCIMB 40716.

Furthermore, the invention provides isolated genes for the production of, and immunity to, lacticin 3147 as deposited in the plasmid pMRC01 above.

The present invention also relates to the use of lacticin 3147 or a lacticin 3147 producing host in the treatment of mastitis in cattle, to prevent clostridial spoilage in cheese, as a food preservative in pasteurised cheeses and cheese spreads, as a shelf-life extender in milk and milk products, in the production of alcoholic beverages particularly in the brewing industry, in vegetable fermentations, by incorporation into canned foods and in meat preservation. Additional uses include incorporation into oral healthcare products such as toothpaste and mouthwashes and in cosmetic treatments for acne. The bacteriocin may be used against Gram negative bacteria which have been treated with chelating agents.

The invention also relates to the use of a plasmid or a gene(s) encoding the lacticin 3147 bacteriocin to confer bacteriocin producing properties on a host such as a bacterium, particularly a cheese-starter culture. The invention also provides a host such as a bacterium containing a plasmid or a gene(s) as defined above, encoding lacticin 3147. The invention also provides a method of producing lacticin 3147 comprising culturing a bacterium containing lacticin 3147-encoding gene(s) and isolating lacticin 3147 from the culture, and a method of conferring lacticin 3147-producing properties on a host such as a bacterium, comprising introducing and expressing in the host a plasmid or gene(s) as defined above encoding lacticin 3147.

The invention also relates to a food-grade genetic marker system comprising genes for immunity to lacticin 3147 as encoded by plasmid pMRC01. The genetic determinants which encode lacticin 3147 immunity may be introduced into a bacterial strain together with any desirable gene(s) which have been linked to them. A bacterial cell which has received the genes can be selected from the general population of cells by plating on medium containing lacticin 3147, since cells containing the lacticin 3147 immunity genes will be able to grow in this environment. Given that spontaneous resistance to lacticin 3147 occurs at a low frequency in lactococcal strains (undetectable for some strains) this marker system should provide all the advantages of well known antibiotics such as Ampicillin and Erythromycin with none of the negative clinical associations. Since these 3147 genes have originated from a GRAS (Generally Regarded As Safe) organism they are considered to be Food Grade.

The invention also provides phage resistance gene(s), particularly gene(s) encoding total resistance to the small isometric-headed phage 712 and burst size limitation for the prolate-headed phage c2. The phage resistance gene(s) may be encoded by the plasmid pMRC01, deposited as described above.

Further the invention relates to a host such as a bacterium containing a plasmid or gene(s) as defined above encoding phage resistance. Also provided is a method of conferring phage resistance on a host such as a bacterium and particularly a cheese starter culture, comprising introducing and expressing therein a plasmid or gene(s) as defined above encoding phage resistance. The invention also relates to the use of a plasmid or phage resistance gene(s) to confer phage resistance on a host such as a bacterium, particularly a cheese-starter culture.

In a further aspect the invention provides *L. lactis* strain DPC2949 as deposited at the National Collection of Industrial and Marine Bacteria, Aberdeen, Scotland on Apr. 11, 1995 under the Accession No. NCIMB 40715, the bacterium-encoding gene(s) thereof and the bacteriocin produced thereby. The invention also relates to methods of preventing late gas-blowing or of controlling non-starter lactic acid bacteria in Cheddar cheese production comprising either the addition of *L. lactis* DPC2949 or the bacteriocin produced thereby to the initial cheese starter culture.

The invention also provides bacteriocin-encoding genes, bacteriocin immunity genes, phage resistance genes, plasmids and strains substantially homologous to those defined above also encoding bacteriocin production and immunity and phage resistance. Such homologous genes, plasmids and strains arise because of the degeneracy of the genetic code, the possibility of replacing one amino-acid with another without affecting the functional characteristics of a protein and the possibility of deleting a non-essential portion of a gene or amino-acid sequence while still producing a functional end-product. The invention also provides genes as defined above linked to other DNA sequences.

Since the biological activity of the bacteriocin of the present invention is similar to that of nisin, it could be used for similar applications. Unlike Northern Europe, many fermented dairy products in Southern Europe are still being made using traditional methods without the use of commercial starters. One source of these strains in Ireland is Buttermilk plants commonly used by Irish housewives in the souring of bread for breadmaking. These Buttermilk plants, also known as kefir grains, are creamy white in colour and resemble cauliflower florets. They are resilient and difficult to break up due to the presence of kefir in a water soluble polysaccharide produced by the lactobacilli in the plant. They are composed of lactococci, leuconostocs, lactobacilli, yeasts and acetic acid bacteria which are held together in a matrix and are recoverable at the end of the fermentation process as a solid mass. Some isolates produce a bacteriocin which may be important in maintaining the integrity of the grain as it is assumed that all other organisms in the grain are resistant to it (Rea & Cogan, 1994).

The present invention will now be described in greater detail with reference to the accompanying drawing in which:

FIGS. 1A and 1B. Cross-Sensitivity Study, a L. lactis DPC3147; b, NCDO496; c. DPC2949; d. DPC3220; e. DPC33(1) were grown on GM17 agar plates and subsequently overlaid with A. DPC3147 and B. NCDO496. Zones where no growth has occurred indicate inhibition of the indicator due to bacteriocin(s) produced by the producer.

FIGS. 2A, 2B, 2C, 2D, and 2E. Protease Sensitivity Assay. Filtered cell-free bacteriocin solution and enzyme solution (A represents control, no enzyme; B, alpha-chymotrypsin; C, trypsin; D, pronase E and E represents proteinase K) were spotted 1 cm apart on GM17 agar plates and subsequently overlaid with the indicator L. lactis strain HP.

FIG. 3. Polymerase Chain Reaction. The 166 bp PCR amplified fragment from genomic DNA isolated from L. lactis NCDO496 is indicated in lane 1. No amplified products are evident where DNA isolated from strains DPC3147, MG1614, and DPC2949 were used as templates. Lane 3 corresponds to DNA molecular weight markers.

Figure 4:
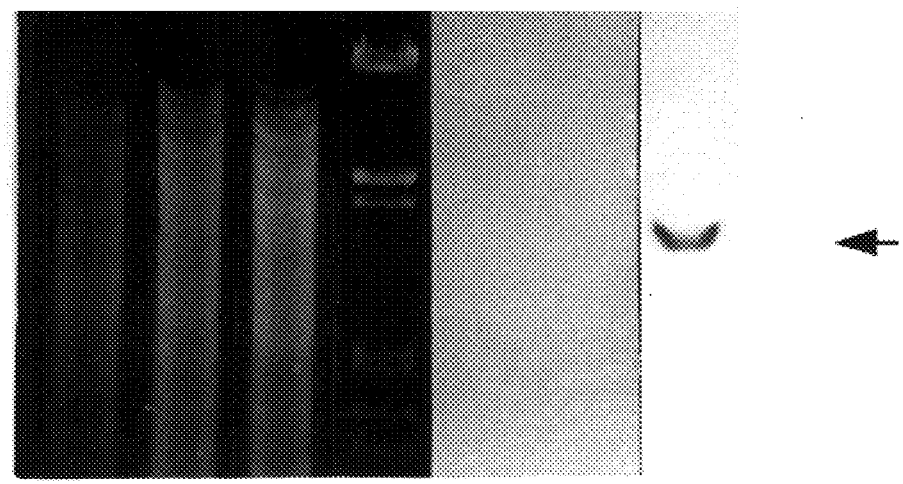

FIG. 4. DNA Hybridization. Hind III restricted genome DNA from L. lactis DPC3147, MG1614, and NCDO496 is shown in lanes 1, 2 and 3 respectively. Lane 4 corresponds to DNA molecular weight markers. The nis A gene probe, hybridized to a 3.5 kb fragment on the NCDO496 genome (lane 3'). No hybridizing DNA is observed in DNA isolated from DPC3147 (lane 1) or from MG1614 (lane 2).

Figure 5:
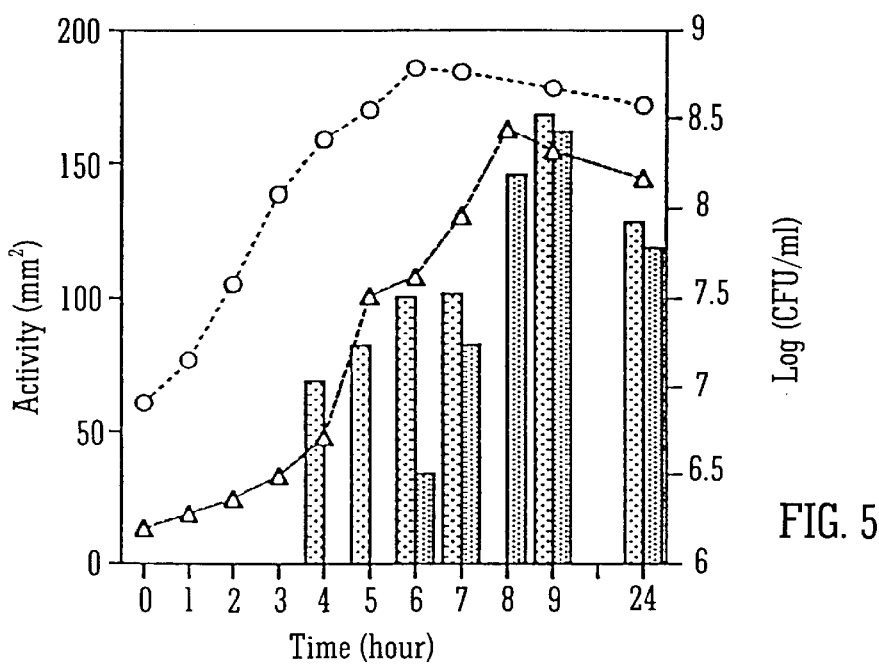

FIG. 5. Growth of L. lactis DPC3147 in GM17 and TYT30 media.

Figure 6:
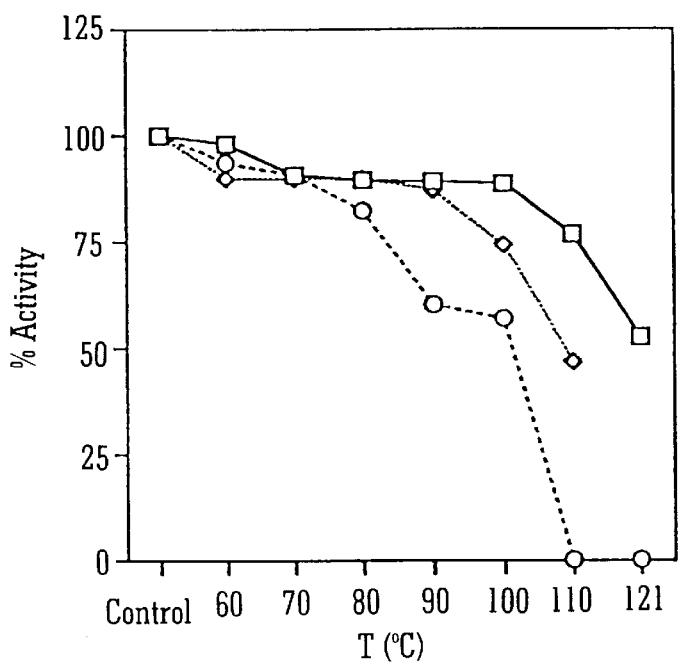

FIG. 6. Effect of heating at 60° C. to 121° C. for 10 minutes on the stability of lacticin 3147 at pH5, pH7, pH9. 100% activity is the activity at pH 5, 7 and 9 with no heating.

Figure 7:
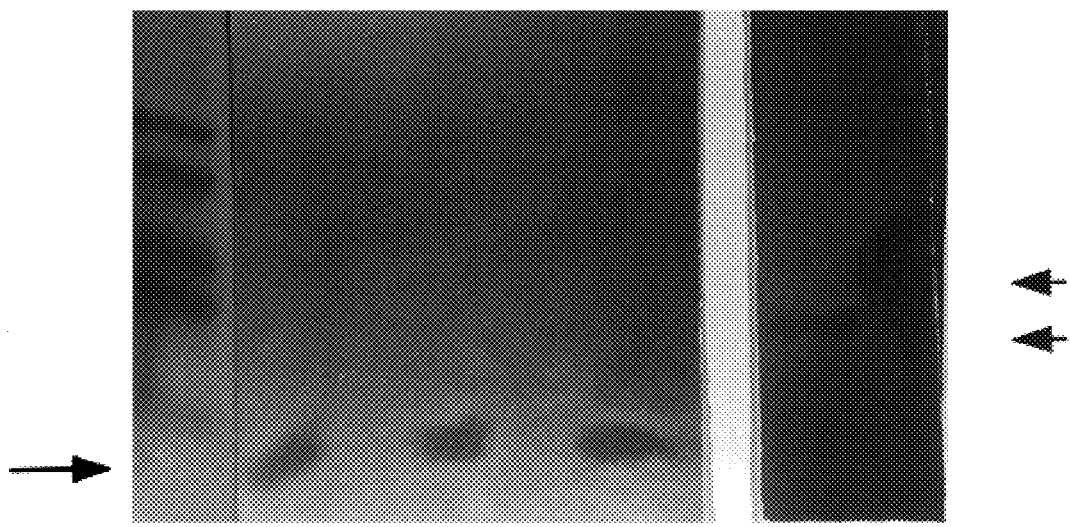

FIG. 7. Overlaid SDS-PAGE gel. Preparations of lacticin 3147 (A. lanes 2, 3 and 4; B. lane 2) and of lactococcin A (B. lane 3) were electrophoresed on a 10% SDS-PAGE gel. This was overlaid with an active culture of L. lactis HP. Inhibition of the indicator is seen as zones in the indicator lawn. Molecular weight markers (2.5 kDa to 17 kDa) are indicated in A. lane 1.

Figure 8:
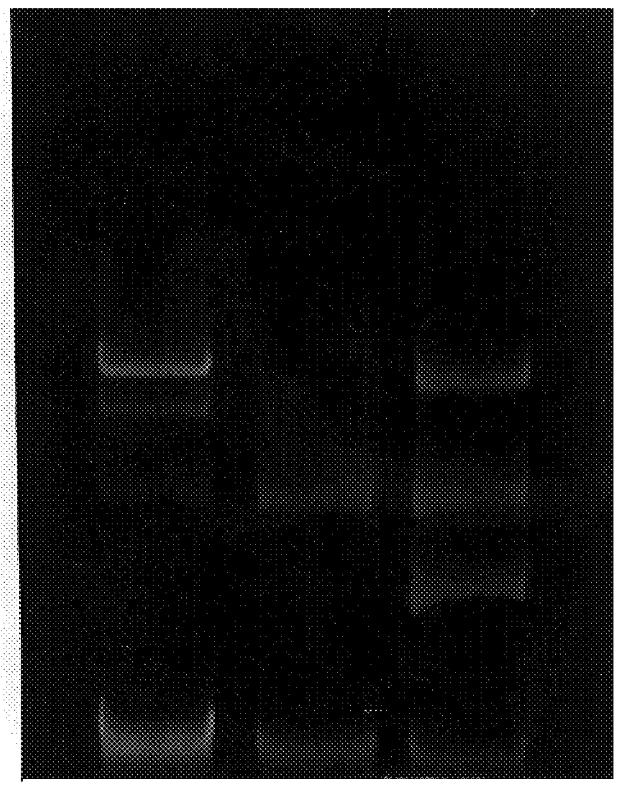

FIG. 8. Analysis of the plasmid complements of a putative transconjugant (lane 2) obtained from a mating between L. lactis DPC3147 (lane 1) and the plasmid-free strain MG1614. The transconjugant contain a 63 kDa plasmid acquired from the DPC3147 donor which is not evident in the plasmid-free MG1614 strain.

Figure 9:
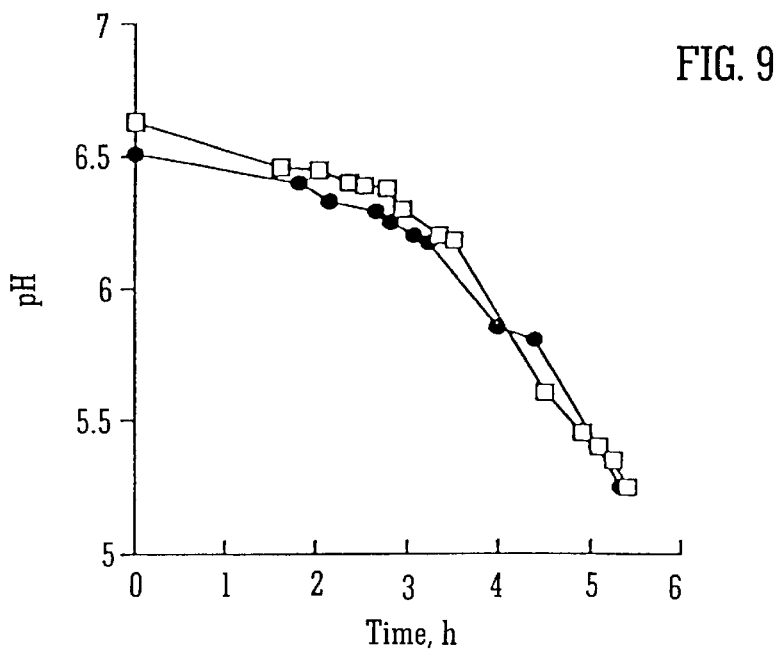

FIG. 9. pH profiles during Cheddar cheese manufacture using the DPC3147 strain as cheese starter.

Figure 10:
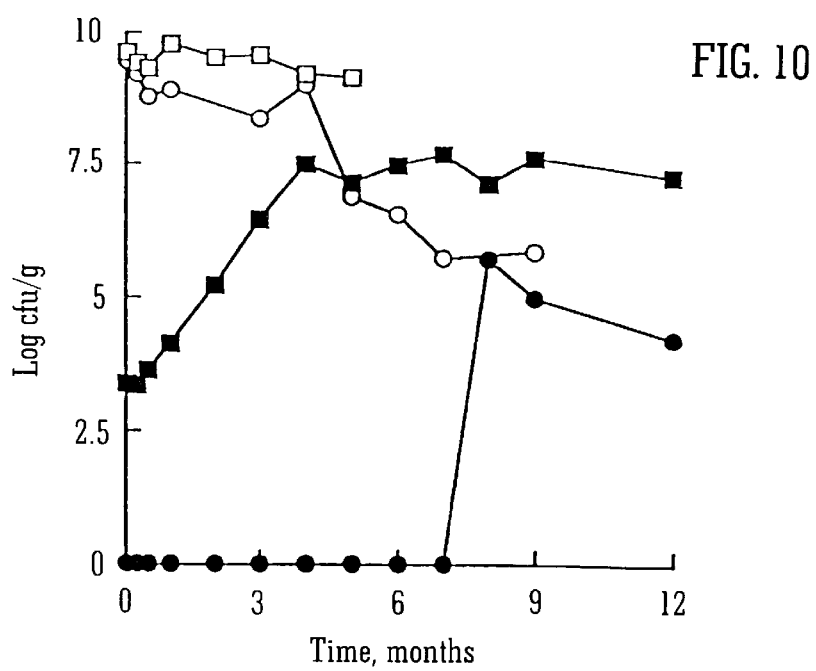

FIG. 10. Growth of starter and NSLAB during ripening of Cheddar cheese using the DPC3147 strain as cheese starter.

FIG. 11. pH profiles during Cheddar cheese manufacture using a transconjugant of strain 303 which produces lacticin 3147 as cheese starter.

FIG. 12. Growth of starter and NSLAB during ripening of Cheddar cheese using a transconjugant of strain 303 which produces lacticin 3147 as cheese starter.

Figure 13A:
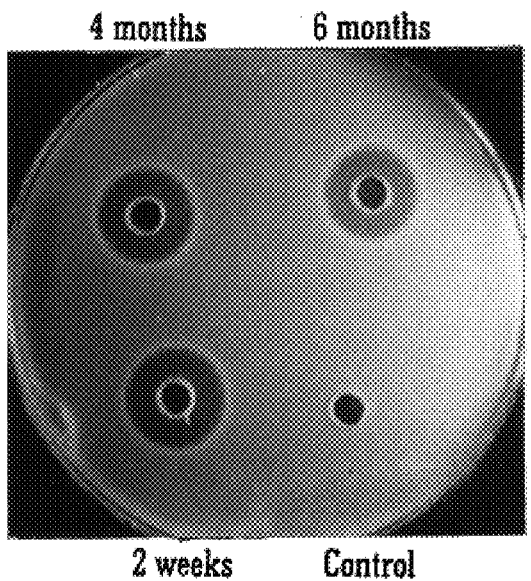

FIG. 13A. Residual Lacticin 3147 activities in Cheddar cheese made with bacteriocin-producing strains (DPC3147, DPC3256 and DPC3204) sampled after 2 weeks, 4 months and 6 months. The commercial strain DPC4268 was used as the control starter.

Figure 13B:
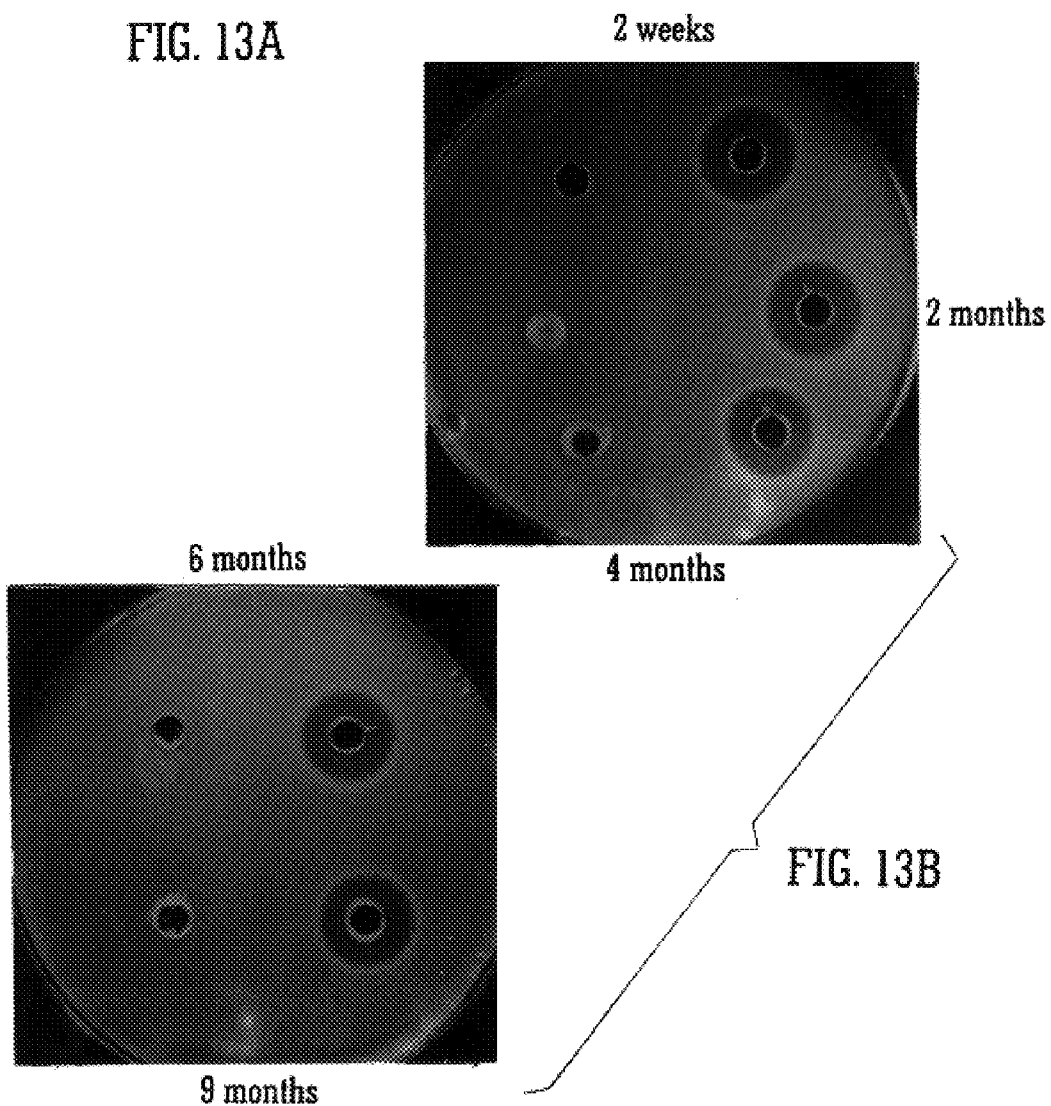

FIG. 13B. Residual lacticin 3147 activity in Cheddar cheese made with the bacteriocin-producing transconjugant DPC4275. Again, DPC4268 was used as the control.

Figure 14A:
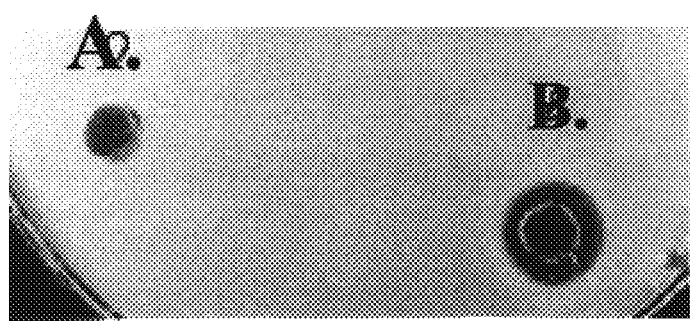

FIG. 14A. Antimicrobial effectiveness of lacticin 3147 requires the presence of Tween Au/ml) has been added.

Figure 14B:
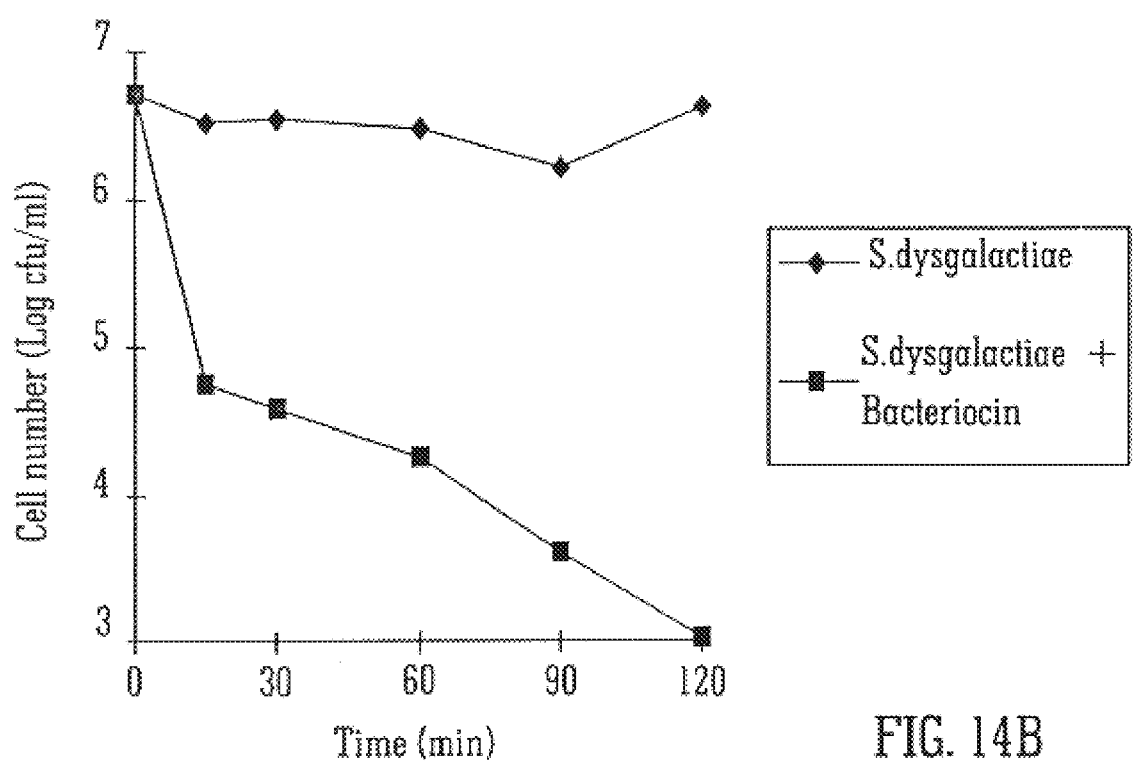

FIG. 14B. Effect of adding lacticin 3147 (10.240 AU/ml) to stationary cells of Streptococcus dysgalactiae.

MATERIALS AND METHODS

A complete list of strains, their growth media and temperature of incubation used throughout this study is included in Table 1. Both L. lactis DPC3147 and DPC3220 were isolated from kefir grains, whereas L. lactis strains NCD0496 and NCD0497, known nisin producers, were obtained from the National Collection of Dairy Organisms (NCDO), National Institute for Research and Dairying, Shinfield, Reading, Berkshire, RG2 9AT, England. The source of each of the indicator organisms tested are also listed in Table 1. *L. lactis cells were routinely propagated at 30° C. in M17* (Difco Laboratories, Detroit, USA) supplemented with 0.5% glucose or lactose. Other media used in this study, as indicated in Table 1, included MRS (Difco Laboratories), BHI (Oxoid Ltd., Hampshire, England), TYP (Tryptone 16 g/l, Yeast Extract 16 g/l, NaCl 2.5 g/l, $K_2HPO_4$ 2.5 g/l). TYT30 (Tryptone 2.5 g/l, Yeast Extract 5 g/l, Tween 20 1 g/l, Glucose 10 g/l, β-glycerophosphate 19 g/l. $MgSO_4 7H_2O$, 0.25 g/l, $MnSO_4 4H_2O$ 0.05 g/l), TSA, (Becton Dickson Microbiology Systems, Maryland, USA), Baird-Parker media (Merck, Darmstadt, Germany); RSM (Reconstituted Skim Milk) and pasteurized whole milk.

To test the sensitivity of a strain to DPC3147, to L. lactis NCD0496 and to L. lactis DPC3220, 10 µl aliquots of a fresh overnight culture of each were first spotted on GM17 agar plates and incubated overnight at 30° C. These plates were then gently overlaid with 3 ml of soft agar seeded with 100 µl of the test strain, so as not to disturb the grown producer. The sensitivity of a strain to each bacteriocin producer was scored according to the diameter of the zone of inhibition surrounding that producer. The scoring system adopted is as follows: 0 to 1 (mm) (−); 1 to 5 mm (+); 5 to 15 mm (++); over 15 mm (+++). All strains were stocked in 40% glycerol and stored at −80° C. Working cultures were stored at 5° C. and transferred periodically.

Plates containing bacteriocin were prepared as follows. A cell-free, sterile bacteriocin solution was obtained from an overnight culture of *L. lactis* DPC3147 grown in GM17 by first centrifuging at 8000 g (Sorvall RC-5B) for 10 min. The resulting supernatant was then sterilized by filtering with Millipore HVLP filters (0.45 um) and tempered to 45° C. An equal volume was then added to double strength GM17 and the plates were poured. Where needed, streptomycin was added to agar at a concentration of 500 µg/ml.

To identify lactose metabolizing bacteria, Lactose Indicator Agar (LIA) was used (Tryptone 20 g/l, Yeast Extract 5 g/l, Lactose 10 g/l, NaCl 4 g/l, Sodium Acetate-anhydrous 1.5 g/l, Ascorbic Acid 0.5 g/l, Gelatin 2.5 g/l, Bromocresol Purple (0.004%). Agar Bacteriological 15 g/l. Sucrose Indicator Agar plates were prepared similarly except that sucrose was substituted for lactose as the carbon source.

Measurement of Bacteriocin Activity:

Bacteriocin activity was estimated using an agar well-diffusion assay essentially as described in Parente and Hill (1992). In the agar well diffusion assay, molten agar (GM17 for lactococci) was cooled to 48° C. and inoculated with overnight cultures of the appropriate indicator strain (200 µl in 25 ml agar). The inoculated medium was rapidly dispensed in sterile Petri-dishes and, after solidification, dried for 30 min under a laminar flow hood.

Wells of a uniform diameter were bored in the agar and sealed with 15 µl of tempered soft agar. Sterile culture supernatant fluids (50 µl) were then dispensed in the wells and the plates were incubated overnight at 30° C. These cell-free solutions of the bacteriocin were obtained as above. The difference between the area of the zone of inhibition (in $mm^2$) and the area of the well was measured to estimate bacteriocin activity.

Protease Sensitivity Assays:

The following enzymes were dissolved in sterile distilled $H_2O$ (SDW) to a final concentration of 50 mg/ml: Trypsin (type II, Sigma Chemical Co., Poole, Dorset, England), alpha-chymotrypsin (type II, Sigma), Proteinase K (Sigma), Pronase E (type XIV, Sigma), Catalase (Sigma). Pepsin was dissolved in 0.02N HCl, also to a final concentration of 50 mg/ml. All enzyme solutions were filter sterilised using disposable filters (Rotrand/Red rim 0.2 µm, Schleicher & Schuell). 20 µl aliquots of filtered cell-free bacteriocin solution and 20 µl of each enzyme solution were spotted 1 cm apart on GM17 agar plates and dried for 30 min. All plates were incubated overnight at 30° C. The plates move subsequently overlaid with the indicator organism. Growth of the producer was evident as a zone of inhibition. Controls included plates with spots of either bacteriocin solution or enzyme solution.

Effect of pH and temperature on bacteriocin stability:

A cell-free bacteriocin was exposed to various pH/temperature treatments. Samples were heated to 60, 70, 80, 90, 100, 110 and 121° C. at pH5, pH7 and pH9 for 10 min. Following treatment, all solutions were rapidly cooled and bacteriocin activity was assayed by the well diffusion method.

Estimation of Molecular Weight:

Samples containing 3147 bacteriocin were loaded on urea-SDS polyacrylamide gels, prepared as described by Swank and Munkres (1971). Molecular weight markers for peptides ranging from 2.5 to 17 kDa (Sigma) were used as a standard. A sample of lactococcin was also included on the gel as another indicator of molecular weight. After electrophoresis at 22 mA for 16 h the gels were divided. One half containing the sample and molecular weight markers was stained according to procedures as recommended by the manufacturers (Hoeffer Scientific Instruments). This essentially involved staining overnight with 0.125% Coomassie Brilliant Blue R250 stain. The following day, the gel was destained with "Destain Solution 1" [Methanol 50% (v/v), Acetic Acid 10% (v/v)] for 5 h and then placed in "Destain Solution 2" [Methanol 5% (v/v), Acetic Acid 7% (v/v)]. The other half of the gel was fixed immediately for 2 h in a solution of 20% (v/v) isopropanol and 10% (v/v) acetic acid. It was then washed in several volumes of deionised water for 4 to 6 h. The gel was placed in a large sterile glass Petri-dish and overlaid with 30 ml of soft tempered agar seeded with 800 µl indicator strain. The plate was incubated overnight at 30° C. and examined for a zone of inhibition (Bhunia et. al., 1987)

Isolation of DNA:

Plasmid DNA from lactococci was isolated by the Anderson & McKay method (1983) as follows. Actively growing lactococci cells were collected as with the previous method by centrifugation for 5 sec. The pelleted cells were then resuspended in 379 µl of solution containing 6.7% sucrose, 50 mM Tris, 1 mM EDTA (pH8) and heated to 37° C. Lysozyme (Sigma), dissolved in 25 mM Tris pH8 was added (96.5 µl), and incubated at 37° C. for 5 min. 48.2 µl 0.25 M EDTA. 50 mM Tris pH8 was then mixed in by gentle vortexing, followed by addition of 27.6 µl of the lysis solution (20% SDS, 50 mM Tris, 20 mM EDTA pH8). The resulting mixture was then incubated for 5 to 10 min at 37° C. to complete lysis after which it was completely clear. The lysate was rigorously vortexed for 30 sec and 3 N NaOH (27.6 µl) added. This was mixed in gently by inversion for 10 min. after which, 49.6 µl of 2 M Tris pH7 was added. This was mixed for a further 3 min by inversion. 71.7 µl of 5 M NaCl was then added and the resulting mixture vortexed. This was extracted once with phenol and once with chloroform isoamyl alcohol (24:1). The DNA was then precipitated on addition of 600 µl isopropanol. Following centrifugation for 10 min. the precipitated DNA was washed once in 70% ethanol, dried and resuspended in 30 µl SDW, all of which was then loaded on the gel.

Genomic DNA was extracted from lactococci according to a modification of the method outlined by Hoffman & Winston (1987) which uses shearing with glass beads to lyse the cells. The strains from which DNA was extracted were grown overnight in 5 ml volumes of the appropriate medium. The cells were collected by centrifuging 2 ml volumes of the cultures for 5 sec. The supernatant was discarded and the remaining pellet was vortexed briefly. The cells were resuspended in 0.2 ml of sterile "Extraction Solution" which consists of 2% Triton X 100, 1% SDS, 100 mM NaCl, 10 mM Tris (pH8) and 1 mM EDTA. Phenol-chloroform (0.2 ml) was then added, followed by 0.3 g of acid-washed glass beads of diameter 0.45 to 0.52 mm (Sigma). The suspension was vigorously vortexed for 2 min and then microcentrifuged for 5 min. The resulting upper aqueous phase was gently transferred into a sterile microcentrifuge tube to which 20 µl of 3 M sodium acetate was added. After a gentle vortex, 600 µl absolute ethanol (−20° C.) was added and the mixed suspension centrifuged for 10 min. Then the pellet was washed in 70% alcohol, dried and finally resuspended in 50 µl SDW. To estimate DNA concentration, a 5 µl sample was electrophoresed on a 0.7% agarose gel with ethidium bromide staining. Alternatively, lactococcal genomic DNA was isolated by a modification of the Anderson & McKay procedure. This was performed identically to the method outlined above except that the alkaline denaturation step was omitted.

Polymerase Chain Reaction:

Amplification of lactococcal DNA was performed by the following method using a Perkin Elmer DNA Thermal Cycler. PCR reactions of 100 µl were set up which contained one-tenth volume 10× buffer (Bioline), 5 mM $MgCl_2$, 200 µM of each of the dNTPs. 1 µM of primer(s) and 1.25 units of Taq DNA polymerase. After overlaying each tube with 100 µl sterilised paraffin oil. 1 µl DNA (isolated as previously described) was added to the reaction. The Taq enzyme was added during the first temperature cycle ("Hot Start") and the DNA was amplified for 35 cycles. Each cycle involved 1 min denaturation at 93° C. followed by an annealing step at 55° C. for 1 min and an extension step of 72° C. for 1 min. Of the final reaction mixture, 10% was analyzed on 1.8% (w/v) agarose (Sigma) gels with ethidium bromide staining.

Restriction of DNA

The isolated genomic DNA from the three *L. lactis* strains. DPC3147 (lacticin 3147 producer), MG1614 (Bac⁻) and NCDO496 (nisin producer) were restricted with Hind III enzyme. Restrictions were carried out in 10× "Cuts-All" buffer containing 200 mM Tris-HCl (pH7.5), 70 mM $MgCl_2$, 1 M KCl and 20 mM β-mercaptoethanol and the entire reaction mix was incubated overnight at 37° C. The DNA samples were run on a 1.8% (w/v) agarose gel at 25V overnight. The DNA fingerprint thus obtained, was examined under ultra-violet light to ensure that sufficient DNA had been restricted before proceeding to the next step.

Southern Blotting

After electrophoresis, the restricted DNA was transferred to a Hybond N⁺ nylon membrane by capillary blotting. The procedure used was that described by Maniatis et al. (1989). Initially, the gel was soaked for 10 min in several volumes of 0.2 N HCl and rinsed briefly in deionised water. The DNA was then denatured by soaking the gel for 45 min in several volumes of 1.5 M NaCl, 0.5 N NaOH with constant gentle agitation. Again, the gel was rinsed in deionised water. To neutralise the gel, it was soaked twice in 1 M Tris (pH7.4), 1.5 M NaCl for 30 min with gentle agitation. After neutralisation, the DNA was transferred to a Hybond N⁺ nylon membrane by capillary action. The membrane, which had been previously immersed in 10× SSC transfer buffer (NaCl 87.65 g/l, sodium citrate pH7.0 44.1 g/l) for 5 min was placed directly over the gel and transfer was allowed proceed for 24 h. After this time, the membrane was removed, dried and baked for 2 h at 80° C.

Hybridization:

Hybridizations were performed according to the "Enhanced Chemiluminescence" ECL Gene Detection System in a Techne Hybridiser HB-1. All hybridizations were carried out at 42° C. as suggested by the manufacturer. The nylon membrane containing the transferred DNA was placed in hybridization buffer (supplied with the ECL kit) at 42° C. and a pre-hybridization was carried out for 15 min. The labelled DNA probe was then added and incubated was allowed to proceed overnight at 42° C. The membrane was then removed from the hybridization solution and washed twice at 42° C. for 20 min with primary wash buffer which consists of Urea 36% (w/v), SDS 0.4% (w/v) and 20× SSC 2.5% (v/v). It was then washed for 5 min at room temperature in secondary wash buffer i.e. 20× SSC 10% (v/v).

Amplified DNA (20 µl) from *L. lactis* NCD0496 was run on a 0.6% (w/v) low melting point Sea Plaque Agarose (FMC) gel. The 166 bp nisin probe DNA amplified from NCD0496 DNA was carefully cut from the gel. Labelling this DNA was achieved as follows. 20 µl DNA labelling reagent was added to an equivalent volume of cooled to 37° C. denatured DNA and mixed thoroughly. 20 µl glutaraldehyde solution was then added and the mixture was incubated for 10 min at 37° C. Labelling reagent and glutaraldehyde solutions were both supplied with the ECL kit. Detection of hybridization signals was performed according to the manufacturers recommendations.

Conjugation:

Conjugations were performed as follows. A conjugal mating was set up using *L. lactis* DPC3147 (bac⁺, bac', strep³) as the donor strain and the plasmid free strain MG1614 (bac⁻, bac³. strep') as the recipient. Both strains were grown to mid-log phase ($OD_{600nm}$ 0.5 to 1). The DPC3147 strain was cultivated in GM17 containing pronase E (50 mg/ml), while MG1614 was grown in GM17 supplemented with streptomycin (500 µg/ml). 1 ml aliquots of these cultures were then centrifuged in a microfuge for 30 sec and the resultant pellets were washed once in 1 ml volumes of GM17. The pellets obtained were resuspended in 25 µl GM17, mixed and spotted on a non-selective GM17 agar plate. Donor and recipient controls were prepared in a similar manner. Following overnight incubation at 30° C. the cultures were resuspended in GM17 broth supplemented with 40% glycerol for long-term storage at −80° C. A serial dilution was carried out on an aliquot of the mating mix which was then plated on selective media. The conjugation frequency was estimated as the number of transconjugants (appearing on selection plates) divided by the number of donor cells. Putative transconjugants were checked for lactose metabolizing activity by streaking on LIA plates. To determine the molecular weight of the plasmid encoding bacteriocin production, plasmid DNA from the transconjugants was isolated by the Anderson and McKay method and was run on a 0.7% agarose gel. *L. lactis* MG1614 was used as a negative control and the plasmid profile of *L. lactis* subsp. *lactis* DRC3 was used as the molecular weight standard.

Preparation of Inocula for Cheese-making Trials:

The selected strains were stored at −80° C., and were sub-cultured once in LM17 broth. At 30° C. overnight and twice in RSM before use. Bulk starters were cultivated in 10% RSM which had been pre-heated to 90° C. for 30 min and cooled to 21° C. before inoculation. All the strains were grown separately at 21° C. for 16 h, mixed in equal proportions and inoculated at the levels shown in Table 2.

Cheesemaking:

Milk was pasteurised (72° C.×15 s) and cooled to 30° C. Cheese was made in circular jacketed stainless steel 500 l vats. The milk was inoculated with cultures at the levels summarized in Table 1. Filter-sterilised rennet (Chr. Hansens Laboratories: 31 ml, diluted in 500 ml sterile distilled water) was added 30 min after addition of the starter and the coagulum was cut approximately 40 min later. The curds and whey were cooked to 38° C. and pitched at pH 6.2. The cheddared curd was milled at approximately pH5.2, salted at a level of 27 g/kg and pressed in 18 kg moulds overnight at approximately 412 kPa. Cheese were vacuum packed and ripened for 12 months at 8° C.

Analysis of Cheese:

Bacteriological analysis: At intervals, cheese were aseptically sampled. Starter cells were enumerated on LM17 agar for 3 days after incubation at 30° C. lactobacilli on LBS agar after 5 days at 30° C. enterococci on Kanamycin aesculin agar (Oxoid) after 24 h at 37° C. and coliform on VRB agar after 24 h at 30° C. Microbiological analyses were single estimations at each sampling time.

Gross composition:

Grated cheese samples (2 weeks old) were analysed for salt, fat, protein and moisture. The pH was measured on a paste prepared by macerating 10 g of grated cheese in 10 ml of distilled water. All values are the average of duplicate analyses.

Proteolysis:

Proteolysis of cheese was monitored by measuring the percentage of total nitrogen soluble in water at pH 4.6 (WSN) or in 5% phosphotungstic acid (PTA-N).

Free amino acids:

Free amino acids were measured in the 12% TCA-soluble fraction of the WSN on a Beckman 6300 Amino Acid Analyser.

Sensory Evaluation:

Cheeses were assessed for flavour at 3, 6, 9 and 12 months by a sensory evaluation panel based on a score of 0–8 (0–1 unacceptable; 2–3 poor; 4–5 acceptable; 6–7 good; 8 excellent).

Assaying bacteriocin directly in cheese samples:

Bacteriocin activity was assayed from cheese samples as follows. Cheese samples were initially macerated in equal volumes of distilled water in a stomacher (Lab-Blender 400) for 15 min and heated to 80° C. for 10 min. Then aliquots of 50 $\mu$l were dispensed in wells and bacteriocin activity calculated as the difference in area of the zone of inhibition (in mm2) and the area of the well (as outlined previously).

Transfer of pMRC01 into lactococcal starter strains:

Initially a conjugation was set up with L. lactis DPC3147 (Lac+, Bac– and Streps) as the donor strain and the plasmid-free antibiotic sensitive L. lactis MG1363 as the recipient. Both strains were grown from an overnight culture for 4 hr at 30° C. in L/GM17. The conjugation was carried out in a ratio of 20:1 of recipient to donor. 1 ml of recipient (MG1363) and 50 $\mu$l of donor (DPC3147) were centrifuged. The donor (Bac+) was washed with LM17 broth and resuspended in 50 $\mu$l of LM17. The donor, recipient and mating mix were spotted onto non-selective GM17 agar plates and allowed to dry. Following an overnight incubation at 30° C. the cultures were harvested from the agar plates and resuspended in 500 $\mu$l of GM17 supplemented with 40% glycerol (for long-term storage at –80° C.). A serial dilution of an aliquot of the mating mix was plated onto selective media (LIA containing lacticin 3147). The conjugation frequency was estimated by dividing the number of transconjugants appearing on the selection plates by the number of donor cells. Transconjugants were not readily visible in this case because the donor Lac+ colonies turn the LIA plate yellow and the Lac– colonies are masked. To overcome this problem colonies were picked off at random and spotted onto LIA and observed for lactose utilisation. The transconjugant resulting from this mating was used as a Food Grade donor on further matings with the commercial lactococcal starters. These matings were carried out similarly to above, but at a ratio if 1:1 (with the exception of strain AM2). In these matings transconjugants were observed as Lac+ colonies in a Lac– background. Putative transconjugants were picked from the mating plates and streaked for purity. They were tested for lacticin 3147 production—which is usually an indicator of the success of the mating and plasmid profiles were prepared to compare the recipient to the transconjugant.

Phage resistance:

The phage resistance of a culture was determined by comparing the transconjugant to the parent strain for resistance to a phage homologous to the parent. Plaque assays were carried out as follows. 0.25 ml of an overnight culture, 0.1 ml of 1M CaCl2 and 0.1 ml of the appropriate phage dilution were added to 3 ml of L/GM17 sloppy agar (0.7% agar). The contents were mixed, poured onto M17 agar and incubated at 30° C. for 18 hr.

Detection of Diacetyl, Citrate and Acetolactate.

The assays were conducted on cells grown in 10%RSM (+0.5% tryptone) at 21° C. and 30° C. for 16 hr and 18 hr (respectively) according to the methods for detection of diacetyl, citrate and acetolactate as described in Prill & Hammer (1938). Marier & Boulet (1958) and Jordan & Cogan (1995) respectively. Each assay was carried out in triplicate and the average presented in Table 5.

Concentration and partial purification of lacticin 3147 for incorporation into teat seals:

TY (Tryptone 2.5 g/L, Yeast Extract 5 g/L, Glucose 10 g/L, b-glycerophosphate 19 g/L, MgSO4.7H2O 0.25 g/L, MnSO4.4H2O 0.05 g/L, pH 6.75) broth was prefiltered (15 filter/liter) with HA (Millipore) filters to remove proteins in the media which would bind to the filters. L. lactis DPC 3147 was then grown overnight in the filtered TY-broth. The culture was centrifuged at 10,000 rpm for 15 minutes and then filtered through HVLP filters (Millipore). The bacteriocin was then bound to HA filters (8 filters/liter) and subsequently harvested from the filters using acetone/5 mM Phosphate-Buffer, pH 7.0 (2:1). The mix was subsequently centrifuged and the acetone removed by evaporation. The resultant bacteriocin preparation was freeze-dried and dissolved in sterile distilled water. This was then assayed as above. To add bacteriocin into the teat seal 17,000 units of the bacteriocin prepared as above was added to the seal in a sterile petri disc. On mixing, the bacteriocin and seal formed as emulsion which was then aseptically transferred to a syringe (Cross Vetpharm).

Effectiveness of lacticin 3147 on Streptococcus dysgalactiae M:

10 $\mu$l from a overnight culture was added to 490 $\mu$l of sterile 50 mM phosphate-buffer. pH 7.0 500 $\mu$l lacticin 3147 (10,000 AU/ml) was then added and plate counts were carried out after 0, 15, 30, 60, 90 and 120 minutes at 37° C. to assess cell viability.

Oral Streptococci:

Four cariogenic streptococcal strains isolated from infected patients were grown overnight at 30° C. in Brain Heart Infusion broth. These strains were obtained from Dr. Ger Fitzgerald, University College Cork. The relative sensitivity of each of these strains to the bacteriocin was then determined in comparison to L. lactis HP.

Results

A number of lactococci which exhibited antimicrobial activities were isolated from kefir grains. Protease sensitivity assays demonstrated that the antimicrobials were bacteriocins, since they could readily be degraded by proteinase K. On the basis of cross-sensitivity assays, these bacteriocin producers could be classified into different groups. Strains from the first group, DPC3147, DPC3153, DPC3215, DPC3400, DPC3204 and DPC3244 exhibited cross-immunity indicating that they all produced the same or a very similar bacteriocin (see FIG. 1). Likewise, strains from the second group, DPC3220 and DPC33(1) also exhibited cross-immunity to each other, but were sensitive to the bacteriocin(s) produced by the first group. Strain DPC2949 defined a third set of producers which exhibited cross-sensitivity to members of the first group.

Subsequently, *L. lactis* DPC3147, *L. lactis* DPC2949 and *L. lactis* DPC3220 were chosen as representatives of each group for further study. Initially, these strains were tested for their ability to inhibit a wide range of organisms. The results of these experiments are given in Table 1. It can be seen that the bacteriocin-producers. DPC3147, DPC2949 and DPC3220 do not inhibit themselves but do however inhibit one another. This indicates that the strains are at least distinct from one another. To reduce the possibility that they may be previously well characterised bacteriocin-producing strains, cross-sensitivity studies were carried out to some well known bacteriocin-producers which were, *L. lactis* CNRZ481, the producer of lacticin 481 (Piard et. al., 1991). *L. lactis* NCDO496 (FIG. 1) and NCDO497, nisin producers, and *L. lactis* subsp. *cremoris* 9B4, the producer of lactococcin A, B and M. Each of the bacteriocin-producing strains in question inhibit these four previously characterized strains very well, with DPC3147 being particularly effective against them. In addition, these four strains effectively inhibited DPC3147, DPC2949 and DPC3220. Based on these observations, it thus appeared that none of the strains DPC3147, DPC2949 and DPC3220 produced either nisin, lacticin 481 nor lactococcin A, B and M.

Spectrum of Inhibition:

The range of organisms inhibited by each of the strains was examined. Given the extensive application which nisin has found in the food industry, the nisin producer NCDO496 was included in this study for comparative purposes. The relative sensitivities of 54 strains to *L. lactis* DPC3147, NCDO496. DPC2949 and DPC3220 are presented in Table 1. All four producers were very effective in inhibiting other lactococci which included a number of cheese-making strains. The range of inhibition exhibited by DPC3220 however, appears limited to lactococci, and as such is described as having a narrow spectrum. In contrast, the bacteriocin produced by DPC3147 has a very broad spectrum of inhibition which closely resembles that of the nisin producer, NCDO496. Without exception, all Gram positive indicator bacteria tested, including lactococci, lactobacilli, enterococci, bacilli, leuconostocs, pediococci, clostridia, staphylococci and streptococci were sensitive to it. Notably, the two clostridial strains tested were particularly sensitive to DPC3147. Indeed, *C. sporogenes* was so sensitive that the entire overlay was inhibited and no actual zone of inhibition could be measured. *C. tyrobutyricum* was also found to be extremely sensitive. The Listeria strains tested, including the pathogenic strain *L. monocytogenes* NCTC5348 were also sensitive to bacteriocin(s) produced by the DPC3147 strain. Overall, the biological activity of the 3147 bacteriocin closely resembled that of nisin. Interestingly, it was found that DPC3147 was significantly more active than the nisin producer against *S. thermophilus* HA. The closely related lactococci were all very sensitive.

In contrast, *L. lactis* DPC2949 has an intermediate spectrum of inhibition lying somewhere between that observed for strains DPC3147 and DPC3220. Like DPC3220, this strain was effective in inhibiting all of the lactococci tested, but in addition, inhibited most of the Lactobacillus and Leuconostoc species. Thus, its biological activity was quite unlike that of lacticin 481 producers. However, as stated above, the DPC2949 strain and *L. lactis* CNRZ481 exhibited cross-sensitivity. Interestingly, this strain also had slight activity against *Escherichia coli* and *Pseudomonas aeruginosa* but it did not show any inhibition against enterococci, Listeria or staphylococci.

Relationship with Nisin:

Although the cross-sensitivity studies suggest that DPC3147 is not a nisin producer, even though their biological activity appears remarkably similar, a number of experiments aimed at probing the relationship between the two bacteriocins were then performed. Protease sensitivity assays demonstrated that the 3147 bacteriocin is sensitive to trypsin, alpha-chymotrypsin, proteinase K and pronase E but not to pepsin (FIG. 2). In contrast, nisin is not sensitive to trypsin but is degraded by alpha-chymotrypsin, pancreatin and subtilopeptidase. As expected, catalase had no effect on the antimicrobial activity of the 3147 bacteriocin thus eliminating the possibility that the antimicrobial activity may be due to hydrogen peroxide. In addition, none of the strains producing lacticin 3147 were capable of fermenting sucrose. This provides additional evidence that this bacteriocin is not nisin, since the genes encoding nisin (nis A) is linked to genes responsible for sucrose catabolism on the nisin-sucrose transposon. Tn5276 (Horn et. al., 1991). Thus, all those Nip$^+$ (nisin-producing) strains studied to date are in addition Suc$^+$ (Sucrose-fermenting). As expected, *L. lactis* NCDO496 was found to be Suc$^+$ while neither the DPC3220 nor DPC2949 strains could utilize sucrose as a fermentable substrate. In addition, the minimum concentrations (MIC) of pure nisin required for inhibition of strains DPC3147 and NCDO496 were determined. It was found that DPC3147 was inhibited at 100 $\mu$g/ml of nisin while NCDO496 was not inhibited until 400 $\mu$g/ml of nisin was added. These differing MIC values of nisin for DPC3147 and NCDO496, together with all of the above results all strongly suggest that the DPC3147 bacteriocin is distinct from nisin.

Initially, certain strains were investigated for their genetic potential to produce nisin by the polymerase chain reaction (PCR). Using the published sequence of the nisin structural gene. Dodd et al (1990), two primers were synthesized which are complementary to sequences occurring proximal to the 3' and 5' ends of the nis A gene. These should amplify a PCR product of 166 base pairs from nis A-containing template DNA. Indeed, an amplified product of approximately that size was consistently amplified from genomic DNA isolated from the NCDO496 (FIG. 3) strain. In contrast, no amplified product was observed when genomic DNA from DPC3147, DPC2949 and DPC3220 was used. The DNA amplified from *L. lactis* 496 representing most of the nis A gene was then used as a gene probe to DNA isolated from lactococcal strains NCDO496, DPC3147, DPC2949 and DPC3220. These DNAs were first digested with Hind III and electrophoresed on a 1% (w/v) agarose gel prior to transfer to a nylon membrane. As shown in FIG. 4, the nis A gene probe hybridised to a 3.5 kb Hind III fragment on the 496 genome. In contrast, no hybridizing DNA was observed in DNA isolated from strains MG1614 nor DPC3147. This suggests that the bacteriocin produced by DPC3147 is not a close homologue of nisin. Given the inhibition spectrum of the bacteriocin produced by *L. lactis* DPC 3147 and the results of the experiments discussed above demonstrating that it was not nisin, it was concluded that DPC 3147 produced a novel, broad-spectrum bacteriocin which was designated lacticin 3147.

Growth of *L. lactis* DPC3147 and production of lacticin 3147 was monitored in GM17 and TYT30 over a 24 hour period. As shown in FIG. 5 higher cell numbers and bacteriocin activity are obtained in GM17, the richer medium. In both media, lacticin 3147 is produced during exponential phase and peaks during early stationary phase. Subsequently, the bacteriocin activity declines gradually during stationary phase. Production was also determined in a variety of different media including MRS, BHI, TYP, RSM and whole milk. Activity (mm$^2$) was measured from the filtered supernatant of an overnight culture. Production was found to be greatest in MRS with an activity of 170 mm$^2$. The activity in RSM and whole milk was 90% and 73% of that found in MRS.

This indicates that lacticin 3147-producing starter cultures could be used to produce lacticin 3147-containing dairy products.

Effect of pH and temperature on bacteriocin stability:

The effect of pH and temperature on the stability of lacticin 3147 was investigated and results are shown in FIG. 6. Three samples of bacteriocin were brought to a pH of 5, 7 and 9 and aliquots of each were subsequently heated to 60° C., 70° C., 80° C., 90° C., 100° C., 110° C. and 121° C. for 10 minutes. The activity at each pH prior to heat treatment was measured and was taken to be 100% for that pH value. From the graphical representation in FIG. 6, it can be seen that lacticin 3147 is heat-stable, particularly at an acid pH. Indeed at pH 5, the bacteriocin survives autoclaving at 121° C. for 10 minutes and at pH 9, maintains more than 50% of its activity up to a temperature of 100° C.

This means that lacticin 3147 has a potential for use in both high-acid and low-acid canned foods. Low-acid foods (pH4.5) should receive sufficient heat treatment to destroy heat resistant spores of pathogenic *C. botulinium*. By adding lacticin 3147 to these foods, it should be possible to reduce the extent of heat-processing required, thus resulting in improved flavour, increased nutritional value and an overall more economical process. Such applications may be particularly beneficial for products such as canned milk puddings where heat penetration is often a problem. Lacticin 3147 could also be potentially used quite successfully in high-acid foods (pH<4.5), given its acid pH optimum. Even though, a substantial proportion of lacticin 3147 is lost on heating to temperatures exceeding 100° C., its efficiency as a food preservative should not be compromized by heat, as heat-treated bacterial spores display greater sensitivity to bacteriocins. Hence, inhibition of such spores would require the same level of active lacticin 3147. For the reasons stated above lacticin 3147 also has a role in meat preservation.

Molecular weight determination:

The molecular weight of lacticin 3147 was estimated by SDS polyacrylamide gel electrophoresis according to the method of Swank and Munkres (1971). As a control, a sample of lactococcin A, which has a molecular weight of 3 kDa was also analyzed. The gel, which was subsequently overlaid with agar seeded with *L. lactis* indicator strain HP is shown in FIG. 7. It can be seen that lacticin 3147 is somewhat smaller than lactococcin A and its molecular weight was estimated at 2.8 kDa. Molecular weight markers ranging from 2.5 to 17 kDa were used as a standard in the other half of the gel.

Genetic studies:

During initial genetic work with lacticin 3147, it was observed that the bacteriocin-producing property was an easily lost trait. Preliminary experiments were attempted to establish if bacteriocin production by DPC3147 was encoded on a conjugally transmissable piece of DNA. These conjugal matings involved using DPC3147 as the donor strain and the plasmid-free strain, *L. lactis* subsp. *lactis* MG1614, which is streptomycin resistant as the recipient. The selection of transconjugants from such matings was achieved using the plasmid-encoded bacteriocin immunity/resistance determinants as a selectable marker. This involved the incorporation of lacticin 3147 into the selective media. Even when plated at a high cell density (up to $10^8$–$10^9$ CFU/ml), *L. lactis* subsp. *lactis* MG1614 sensitive cells failed to grow on such media, indicating a very low level of spontaneous resistance occurring for this strain to the 3147 bacteriocin. The incorporation of lacticin 3147 into selective media may thus form the basis for a novel food-grade marker system for use in genetic manipulation of lactococci. In matings involving strains MG1614 and DPC3147, putative transconjugants (bac$^{imm}$.strep'), were isolated at a frequency of $10^{-3}$ per donor cell. These cells were subsequently found to be lactose deficient and also had acquired the ability to produce bacteriocin. As expected, these putative transconjugants exhibited cross-immunity to DPC3147 and also, could inhibit a wide range of Gram positive bacteria. Evidence that these actually represented true transconjugants was obtained on analysing their plasmid complements. In all cases, the bac$^-$, bac$^{imm}$.strep' cells had acquired a 63 kDa plasmid, designated pMRC01. A similar sized plasmid is clearly evident in plasmid profiles of the DPC3147 strain (FIG. 8). This indicates that the genetic determinants encoding lacticin 3147 are encoded on the pMRCO1 conjugative plasmid. Furthermore, similar numbers of colonies were obtained from the mating when plated on media containing streptomycin and bacteriocin, and when plated on media containing streptomycin solely. Moreover, when these strep' colonies were overlaid with strain MG1614, all were observed to be bac$^+$. This would suggest that all those MG1614 cells which had not received the plasmid during mating had been killed off by lacticin 3147 produced by DPC3147 in the mating mix. This would negate the requirement for incorporating bacteriocin to select transconjugants in such matings.

Mastitis:

Since lacticin 3147 was shown to be effective in inhibiting *S. aureus* ATCC25923 and *S. thermophilus* HA and ST112 (Table 1), a separate study was initiated to investigate its ability to inhibit a variety of clinical isolates obtained from mastitic animals. These virulent bacteria were obtained from the Department of Dairy Husbandry, Teagasc, Moorepark, Fermoy, Co. Cork. In all six streptococci and ten staphylococci were tested. DPC3147 was most effective against these pathogenic strains, as shown in Table 3. All the streptococci, except *S. dysgalactiae* strain M were quite sensitive to it as were all the staphylococci, except strain 12. A similar outcome was seen with NCDO496, although in some cases DPC3147 is slightly more successful against the streptococci. DPC3220 does not display any activity against either the streptococci or the staphylococci.

In general the streptococcal strains were more sensitive to DPC3147 that the staphylococcal strains whereas the reverse is true for the nisin producers NCDO496 and NCDO497. This suggests that it would be particularly effective to use lacticin 3147 in combination with another bacteriocin, such as nisin, as a mastitis treatment. In such a situation it is much less likely that the infecting organisms would develop resistance to both bacteriocins. Clearly, the use of bacteriocins in the treatment of mastitis may mean that milk would not have to be withheld as would be the case with an antibiotic-based treatment.

Phage Resistance:

The conjugal plasmid, pMRC01, also conferred an increased level of phage resistance to *L. lactis* subsp. *lactis* MG1614. In contrast to the MG1614 parent, transconjugants containing the plasmid exhibited total resistance to the small isometric-heated phage 712. In addition, the burst size of prolate headed phage c2 appeared drastically reduced (as evidenced by pinpoint plaques). Further studies demonstrated that the resistance mechanism encoded by the pMRCO1 plasmid did not affect the ability of phage to adsorb to the cells, nor did it appear to inhibit phage DNA replication once the infecting phage DNA was internalised inside the host. Consequently, the life cycle of the phage was inhibited at some point after phage DNA replication had occurred. This potent phage resistance mechanism was thus assumed to be an abortive infection (or Abi) mechanism.

In lactococci catabolism of lactose is usually plasmid-linked. Therefore, the plasmid-free strain *L. lactis* subsp. *lactis* MG1614 cannot ferment lactose. Since MG1614 transconjugants containing the multifunctional pMRCO1 are also lac deficient, this would suggest that the genes necessary for lactose catabolism are not encoded by pMRCO1 plasmid. MG1614 containing pMRCO1 was then mated with a lactococcal cheese starter strain HP. Putative transconjugants were selected from such matings based on their ability to ferment lactose and become resistant to lacticin 3147. These lac⁻ cells also now produced lacticin 3147 and had also become totally resistant to phage which normally infect the HP strain. Examination of the plasmid complements of these strains revealed that they had acquired an extra plasmid of 63 kb, the size of pMRCO1. This demonstrates that bacteriocin linked phage resistance may prove to be a very efficient method in the improvement of commercial cheese starters.

These results indicate that lacticin 3147 producers may actually be used as cheese starter strains rather than adding a bacteriocin preparation as with nisin. The primary advantage of this is that by directly adding the producing strain, food additive legislation may be overcome as there is no restriction on the use of the strain itself.

Cheese-Making Trials:

Problems associated with nisin producing starters include such undesirable characteristics as an inability to produce sufficient acid for cheesemaking, that they are usually proteinase deficient and also that they are phage sensitive. As outlined above the latter characteristics are not associated with lacticin 3147 producers since bacteriocin functions and phage resistance are linked on pMRCO1. To test the ability of such strains to act as cheese starters two separate cheese trials were performed. In the first, three strains were used, one of which was strain DPC3147. The other two, DPC3204 and 3256 are also kefir isolates, both of which exhibit crossimmunity with DPC3147. Consequently, these are lacticin 3147 producers as well. As illustrated in FIG. 9, these strains produced acid much like the fast acid commercial strain 303 during cheesemaking. Thus it can be concluded that with regard to acid production these strains make acceptable starters. During cheddar cheese ripening non-starter lactic acid bacteria (NSLAB) can reach levels exceeding $10^7$ cfu/g. Since these can be mainly lactobacilli, it was important to investigate their growth or otherwise in cheese made with lacticin 3147 producers (remembering that lacticin 3147 inhibits all lactobacilli tested). As shown in FIG. 10, no NSLABs were detected in cheese made with the bacteriocin-producing strains even after six months (the average duration of cheddar ripening). In contrast, NSLABs had reached levels of $10^{7.5}$ cfu/g after approximately 4 months in controls produced without the bacteriocin. In the second cheese trial, a transconjugant of strain 303 which produces lacticin 3147 was used as a starter with 303 again as the control strain. The results shown in FIG. 11 again demonstrate that the 303 transconjugant performed satisfactorily as a starter during cheese manufacture. In addition the NSLAB levels appearing in the cheese made in this trial (FIG. 12) were significantly lower (in excess of 100-fold) than in the control cheese. Sensory analyses subsequently demonstrated that there were no major differences in flavour and aroma between the two cheeses.

NSLAB which are found in ripening cheese may contribute to the flavour of the cheese. It would be possible to use lacticin 3147 or a commercial starter strain producing it to control the entire microbial population of a cheese, thus allowing the flavour of a cheese to be designed.

Lacticin 3147 was found to be particularly active against *Clostridia tyrobutyricum* and *C. sporogenes*. It is well established that the outgrowth of milk-contaminating anaerobic spore-formers such as *C. tyrobutyricum* and *C. butyricum* is primarily responsible for the problem of late-gas blowing in some cheeses i.e. the formation of hydrogen gases and carbon dioxide during ripening resulting in the development of large holes. These bacteria convert lactic acid into butyric acid giving rise to off-flavours and aromas. Thus, lacticin 3147 also has a use in such products given its potency against clostridial strains.

The introduction of this genetic material into lactococcal industrial strains introduces complications regarding the availability of food-grade selection markers, and the possibility of the loss of industrially important plasmid-encoded functions such as lactose fermentation, proteolytic activity, bacteriophage resistance and citrate utilization. In this regard lacticin 3147 production and immunity may be incorporated as a desirable phenotype of some industrial starter cultures used in many commercial applications. The results described here demonstrate that incorporation of this bacteriocin as a selectable marker into the media itself can form the basis for a novel selectable system. The gene(s) encoding immunity to lacticin 3147 can be linked to desirable traits on plasmids and transconjugants containing these plasmids would then selectively grow on bacteriocin-producing media. It has been observed that the level of spontaneous resistance to lacticin 3147 by some commercial cheese making strains is very low and additionally, plasmid maintenance by pMRC01-containing strains would be assured in fermentations since cells which lose the plasmid would be killed by the lacticin 3147 produced, both properties which are required for an effective selectable system. This is a significant advantage as most selectable markers to date are not of food-grade quality. Indeed, most are actually antibiotics which cannot be used because of the danger of the occurrence of antibiotic resistant strains of clinical importance.

Strain DPC2949:

The biological activity exhibited by *L. lactis* DPC2949 was quite similar to that of the previously characterized *L. lactis* CNRZ481 in that common sensitive strains include lactococci, *Clostridium tyrobutyricum*, Leuconostoc and some, but not all lactobacilli. In addition, *Bacillus substilis*, *Enterococcus faecalis*, *Listeria innocua* and *L. monocytogenes* were not inhibited by either bacteriocin producer. However, cross-sensitivity studies indicated that they were actually different since both inhibited each other. Unexpectedly, DPC2949 gave slight inhibition of the two Gram negative strains *Escherichia coli* and *Pseudomonas aeroginosa*. Strain DPC2949 thus produces an intermediate spectrum bacteriocin which has applications such as the prevention of late gas-blowing in Cheddar cheese. It could also be applied to the control of non-starter lactic acid bacteria (NSLABs) and consequently, to assess their effect on Cheddar cheese quality, which still remains to be established.

Cheese-Making Trials:

As stated previously, cheese made with lacticin3147-producing starters had significantly less non-starter lactic acidbacteria (NSLABs) in them when compared to corresponding cheese made with a commercial starter. Since then we have assayed the bacteriocin in these cheeses. In Cheese trial 1 the presence of lacticin 3147 in take test cheese was confirmed (using *L. lactis* AM2 as the indicator strain) at a level of approximately 1.280 AU/ml which remained constant in the cheese over the 28-week ripening period (FIG. 13A). In contrast, no anti-microbial activity was detected in the control cheese. Similarly, the amount of bacteriocin detected in cheese trial 2 was approximately 1.280 AU/ml which also remained constant over the ripening period (FIG. 13B). Thus the level of bacteriocin observed in the cheese corresponds to the number of NSLABs which occur in the cheese during ripening.

Genetic studies:

To evaluate the potential usefulness of the lacticin 3147-encoding plasmid (pMRC01) for starter strain improvement it was transferred into a variety of lactococcal strains including those currently used for Cheddar cheese and lactic butter manufacture. These transfers were performed in a Food Grade manner via conjugations (bacterial matings) after which the newly modified strains were selected based on their immunity to the bacteriocin. Such matings first necessitated the construction of a Food Grade donor strain for the plasmid which is sensitive to antibiotics. Depending on the starter recipient used one of three possible results for each of the matings was recorded. In the first, starters were isolated which had improved phage resistance properties and produced (and were resistant to) bacteriocin (Table 4). Genetic analyses confirmed that they had received the pMRC01 plasmid which could efficiently be mated back out of the strain.

These strains retained their commercially important characteristics for example ability to produce acid (for cheese starters) and/or diacetyl (for lactic butter production, Table 2). In addition, the plasmid appeared stable in these strains and was maintained over a number of successive subcultures. One such strain was subsequently used for pilot-scale Cheddar cheese manufacture. Another result of these conjugations was the identification of strains which produced the bacteriocin but had not improved phage resistance. Genetic analysis of one such strain demonstrated that such a phenotype was associated with plasmid co-integration in this strain. Lastly, a number of strains were found to be recalcitrant to the pMRC01 plasmid. One possible explanation for this observation is that the plasmid maybe incompatible with a resident plasmid of the strain (e.g. pMRC01 was found to be incompatible with the lactococcal plasmid pNP40 in this study). The overall significance of the results of these matings can be summarized as follows: 1) The genetic determinant(s) encoding immunity to lacticin 3147 is very useful as a food grade selectable marker for starter strain improvement. The lactococcal strains tested in this study proved very sensitive to the bacteriocin incorporated in solid media unless they had received the bacteriocin genes. Indeed, the bacteriocin is as convenient to use as conventional antibiotics for such studies. 2) A number of new starter strains have now been generated using the bacteriocin. Many of these have also been improved with regard to their phage resistance. Importantly all these new strains now produce the bacteriocin and may be used as starters for products where the bacteriocin might impart a desirable effect. Examples include reduction of NSLAB numbers in cheese products or elimination of undesirable bacteria from some fermented meat and fish products.

Mastitis:

As a result of the growing concern over the use of antibiotics for the treatment and prevention of disease in animals the potential of using lacticin 3147 in the prevention of bovine mastitis was investigated. To achieve this the bacteriocin was incorporated into teat seals preparations. These seals are manufactured by Cross Vetpharm (Broomhill Road, Tallaght, Dublin 24. Ireland) and act as a physical barrier in the cow against infection. The bacteriocin provides an additional anti-microbial barrier over the physical one provided by the seal itself. Incorporation of the bacteriocin into the teat seals first required the preparation of the bacteriocin in a highly concentrated and semi-purified form. The anti-microbial effectiveness of lacticin 3147 in the environment of the seal required the addition of either Tween 20 or 80 in concentrations of 2% (FIG. 14A). Where the detergent was not present negligble bacteriocin activity was recorded in the treated seals. Having successfully prepared effective bacteriocin-containing teat seals a number of animal trials were then performed. These involved exposure of the modified seals to the animal for different time periods after which the seals were removed. Overall such studies have demonstrated that the animals tolerated the bacteriocin-containing seals as evidenced by low associated somatic cell counts. In addition, seals extracted from the animal were later shown to retain bacteriocin activity. Since lacticin 3147 was found to inhibit a range of mastitic streptococci its effectiveness on Streptococcus dysgalactiae M, a strain previously isolated from an infected animal, was studied. Addition of the bacteriocin (10.240 AU/ml) to stationary phase cells of this strain resulted in a 99.99% kill in just 2 hours (FIG. 14B). Other aspects of this study focused on the frequency at which a mastitic strain can develop resistance to lacticin 3147 since this could limit its practical usefulness as an effective antimicrobial under certain conditions. However, only 0.003% bacterial cells of the M strain developed increased tolerance to the bacteriocin after prolonged exposure.

Inhibition of Oral Streptococci:

A number of oral streptococci have also been tested for sensitivity to lacticin 3147 to investigate the use of the bacteriocin in such applications as mouth washes, dental products etc. The strains tested include four cariogenic streptococci isolated from infected patients. All four strains tested proved sensitive to the bacteriocin (12.5% as sensitive as *L. lactis* HP). Importantly, fermented dairy products manufactured with lacticin 3147-producing starters may therefore have additional anti-cariogenic characteristics.

TABLE 1

Inhibition Spectrum of *Lactococcus lactic* DPC3147, *L. lactis* NCDO496 and *L. lactis* DPC3200

| | | Sensitivity | | | | |
|---|---|---|---|---|---|---|
| Strain | Medium | DPC 3147 | NCDO 496 | DPC 2949 | DPC 3220 | Source |
| *Acetobacter acetii* | UB[1] | + | + | + | NZ | DPC |
| *Acetobacter suboxydons* | UB[1] | NZ | NZ | NZ | NZ | DPC |
| *Bacillus cereus* ATCC9139 | GM17[2] | + | + | NZ | NZ | DPC |
| *Bacillus subtilis* BD630 | TYP[2] | + | + | NZ | NZ | DPC |
| *Clostridium sporogenes* NCFB1791 | RCM[3] | +++ | +++ | NZ | NZ | DPC |
| *Clostridium tyro-* | RCM[3] | +++ | +++ | +++ | NZ | DPC |

TABLE 1-continued

Inhibition Spectrum of *Lactococcus lactic* DPC3147, *L. lactis* NCDO496 and *L. lactis* DPC3200

| Strain | Medium | Sensitivity DPC 3147 | NCDO 496 | DPC 2949 | DPC 3220 | Source |
|---|---|---|---|---|---|---|
| *butyricum* NCFB1755 | | | | | | |
| *Enterococcus faecium* NCDO942 | GM17[2] | ++ | ++ | − | NZ | NCDO |
| *Enterococcus faecalis* | | | | | | |
| NCDO610 | GM17[2] | ++ | + | NZ | NZ | DPC |
| 10Cl | GM17[2] | ++ | + | NZ | NZ | DPC |
| NCDO581 | GM17[2] | +++ | + | NZ | NZ | |
| *Lactobacillus acidophilus* ATCC4356 | MRS[2]* | + | + | ++ | NZ | ATCC |
| *Lactobacillus bulgaricus* ATCC11842 | MRS[4]* | ++ | ++ | NZ | NZ | ATCC |
| *Lactobacillus casei* ATCC334 | MRS[2] | ++ | ++ | − | NZ | ATCC |
| *Lactobacillus curvatus* CNRZ117 | MRS[2] | + | ++ | NZ | NZ | CNRZ |
| *Lactobacillus fermenticum* ATCC9338 | MRS[2]* | +++ | +++ | + | NZ | ATCC |
| *Lactobacillus helveticus* | | | | | | |
| NCDO257 | MRS[2]* | +++ | ++ | + | NZ | NCDO |
| NCDO1209 | MRS[2]* | +++ | ++ | ++ | NZ | NCDO |
| NCDO1244 | MRS[2]* | +++ | +++ | ++ | NZ | NCDO |
| ATCC15009 | MRS[2] | ++ | ++ | + | NZ | ATCC |
| *Lactobacillus kefir* NCFB2737 | MRS[3] | +++ | ++ | + | NZ | NCFB |
| *Lactobacillus leichmanii* | | | | | | |
| NCDO299 | MRS[2]* | +++ | ++ | ++ | NZ | NCDO |
| NCDO302 | MRS[2]* | +++ | +++ | + | NZ | NCDO |
| *Lactobacillus reuteri* DSM20016 | MRS[2] | ++ | ++ | NZ | NZ | DPC |
| *Lactobacillus sake* NCFB2714 | MRS[3]* | +++ | +++ | ++ | NZ | NCFB |
| *Lactococcus lactis* | | | | | | |
| DPC3147 | GM17[3] | NZ | + | ++ | ++ | DPC |
| NCDO496 (nisin producer) | GM17[3] | ++ | NZ | ++ | ++ | NCDO |
| NCDO497 (nisin producer) | GM17[3] | +++ | NZ | ++ | ++ | NCDO |
| DPC2949 | GM17[3] | +++ | + | NZ | NZ | DPC |
| DPC3220 | GM17[3] | +++ | + | ++ | NZ | DPC |
| DPC33(1) | GM17[3] | +++ | + | NZ | NZ | DPC |
| AM2 | GM17[3] | +++ | +++ | ++ | ++ | DPC |
| CNRZ481 | GM17[3] | +++ | +++ | ++ | +++ | CNRZ |
| 303 | GM17[3] | ++ | ++ | ++ | ++ | DPC |
| HP | GM17[3] | +++ | +++ | ++ | +++ | DPC |
| 9B4 | GM17[3] | +++ | +++ | + | ++ | DPC |
| 938 | GM17[3] | +++ | +++ | + | + | DPC |
| DPC147 | GM17[3] | +++ | +++ | ++ | +++ | DPC |
| DPC712 | GM17[3] | +++ | +++ | ++ | ++ | DPC |
| SK11G | GM17[3] | +++ | +++ | +++ | +++ | DPC |
| 290P | GM17[3] | +++ | ++ | ++ | ++ | DPC |
| DRC3 | GM17[3] | +++ | ++ | ++ | +++ | DPC |
| *Leuconostoc* CNRZ1091 | MRS[2]* | ++ | +++ | + | NZ | CNRZ |
| *Listeria innocua* BD86/26 | GM17[3] | ++ | ++ | NZ | NZ | DPC |
| *Listeria monocytogenes* NCTC5348 | GM17[2] | + | ++ | NZ | NZ | DPC |
| *Pediococcus pentriceans* | | | | | | |
| NCDO992 | GM17[3] | ++ | ++ | NZ | NZ | NCDO |
| NCDO1850 | GM17[3] | + | ++ | NZ | NZ | NCDO |
| *Pediococcus pentosaceus* FBB63 | GM17[3] | ++ | ++ | + | NZ | DPC |
| *Staphlococcus aureus* | TYP[2] | + | + | NZ | NZ | DPC |
| ATCC25923 | | | | | | |
| *Streptococcus thermophilus* | | | | | | |
| HA | GM17[4] | ++ | + | + | NZ | DPC |
| ST112 | GM17[4] | ++ | ++ | NZ | NZ | DPC |
| *Salmonella typhi* | TSA[2] | NZ | NZ | NZ | NZ | DPC |
| *Escherchia coli* | GM17[3] | NZ | NZ | + | NZ | DPC |
| *Pseudomonas aeroginosa* | GM17[1] | NZ | NZ | + | NZ | DPC |

[No Zone (NZ); 0 to 1 mm (−); 1 to 5 mm (+); 5 to 15 mm (++); 15 mm over (+++)]
Temperature of Incubation: [1]21° C.; [2]37° C.; [3]30° C.; [4]42° C.
DPC3147 produces lacticin 3147; NCD0496 produces nisin; DPC3220 produces a bacteriocin with a narrow spectrum of inhibition.

TABLE 2

Strains and levels of inocula used in cheesemaking

| Vat | DPC number | Country of origin | Source | Inoculation rate (v/v %) |
|---|---|---|---|---|
| 1[a] | 303 | — | Chr. Hansens Lab. | 1 |
| 2[a] | 3147 | Ireland | Kefir | 0.7 |
| | 3204 | Ireland | Kefir | 0.7 |
| | 3256 | Ireland | Kefir | 0.7 |
| 1[b] | 303 | — | Chr. Hansens Lab. | 1 |
| 2[b] | 303 (pMRC01) | Ireland | DPC | 1 |

[a]Trial 1.
[b]Trial 2

TABLE 3

Sensitivity of mastitic strains of *Streptococci* and *Staphylococci* to *Lactococcus lactis* DPC3147, *L. lactis* NCDO496 and *L. lactis* DPC3220

| Strain | Medium | Sensitivity DPC 3147 | NCDO 496 | NCDO 497 | DPC 2949 | DPC 3220 |
|---|---|---|---|---|---|---|
| *Streptococcus agalactiae* (B) | GM17 | ++ | ++ | NZ | + | NZ |
| *Streptococcus agalactiae* (H) | GM17 | ++ | + | ++ | NZ | NZ |
| *Streptococcus agalactiae* (P) | GM17 | ++ | + | + | NZ | NZ |
| *Streptococcus dysagalactiae* (M) | GM17 | NZ | − | − | NZ | NZ |
| *Streptococcus faecalis* (I) | GM17 | ++ | ++ | NZ | NZ | NZ |
| *Streptococcus uberis* (L) | GM17 | ++ | + | + | NZ | NZ |
| *Staphylococci subspecies* | | | | | | |
| 2 | TSA | + | ++ | ++ | NZ | NZ |
| 11 | TSA | + | ++ | ++ | NZ | NZ |
| 12 | TSA | − | ++ | ++ | NZ | NZ |
| 13 | TSA | + | ++ | ++ | NZ | NZ |
| 89 | TSA | + | ++ | ++ | NZ | NZ |
| 10 | TSA | + | ++ | ++ | NZ | NZ |
| 1 | TSA | + | ++ | ++ | NZ | NZ |
| 22 | TSA | + | ++ | ++ | NZ | NZ |
| 32(a) | TSA | + | ++ | + | NZ | NZ |

TABLE 3-continued

Sensitivity of mastitic strains of Streptococci and Staphylococci to
Lactococcus lactis DPC3147. L. lactis NCDO496 and L. lactis DPC3220

| Strain | Medium | DPC 3147 | NCDO 496 | NCDO 497 | DPC 2949 | DPC 3220 |
|---|---|---|---|---|---|---|
| | | | | Sensitivity | | |
| 36 | TSA | + | ++ | ++ | NZ | NZ |

[No Zone (NZ); 0 to 1 mm (−); 1 to 5 mm (+); 5 to 15 mm (++); 15 mm over (+++)]
DPC3147 produces lacticin 3147; NCDO496 produces nisin; DPC3220 produces a bacteriocin with a narrow spectrum of inhibition.
Temperature of Incubation = 37° C.

TABLE 4

Conjugation results for mating pMRC01 into a variety of
Lactococcus lactis starter recipients

| L. lactis Recipient | Transfer pMRC01 | Mating frequency (per donor) | Improved phage resistance | Mating back out* |
|---|---|---|---|---|
| DPC4268 | + | $2.3 \times 10^{-3}$ | − | − |
| DPC4272 | + | $1.06 \times 10^{-5}$ | − | + |
| DPC4273 | + | $1.03 \times 10^{-4}$ | − | − |
| DPC4274 | + | $4.0 \times 10^{-5}$ | + | + |
| DPC220 | + | $5.4 \times 10^{-4}$ | + | + |
| DPC429 | + | $1.7 \times 10^{-8}$ | + | + |
| HP | + | $6.0 \times 10^{-6}$ | + | + |
| 712 | + | $1.0 \times 10^{-5}$ | + | + |
| ML8 | + | $5.5 \times 10^{-4}$ | + | + |
| 077 | + | $1.1 \times 10^{-5}$ | − | + |
| 007 | + | $1.3 \times 10^{-7}$ | ? | + |

Transconjugants tested exhibit similar acid production to the parents and all were lacticin 3147 producing.
*Mating of transconjugant with L. lactis MG1614.

TABLE 5

Diacetyl and acetolactate production by
L. lactis DPC220 and L. lactis DPC220 containing
pMRC01 (220 TcA)

| Culture | Diacetyl Production (mM ± SD) | Acectolactate Production (mM ± SD) |
|---|---|---|
| DPC220 | 0.218 ± 0.001 | 3.237 ± 0.04 |
| 220 TcA | 0.235 ± 0.017 | 3.616 ± 0.283 |

Citrate utilisation = 100% for all the test cultures.
10% RSM + 0.5% tryptone at 30° C.

References

Anderson, D. G., and L. L. McKay, 1983, Simple and rapid method for isolating large plasmid DNA from lactic streptococci. Appl. Environ. Microbiol. 46:549–552.

Bhunia, A. K., M. C. Johnson, and R. Ray, 1987, Direct detection of an antimicrobial peptide of Pediococcus acidilactici on sodium dodecyl sulfate-polyacrylamide gel electrophoresis. J. Indus. Microbiol. 2:319–322.

De Vuyst L., and E. J. Vandamme, (ed), 1994, Bacteriocins of Lactic Acid Bacteria: Microbiology, Genetics and Applications. Blackie Academic and Professional.

Dodd, H. M. N. Horn, and M. J. Gasson, 1990, Analysis of the genetic determinants for production of the peptide antibiotic, nisin. J. Gen. Microbiol. 136:555–566.

Gratia, A. 1925, C. R. Seanc, Soc. Biol. 93:1040 in Mayr-Harting et. al. 1972.

Gross, E., and J. L. Morell, 1971, The structure of nisin. J. Am. Chem. Soc. 93:4634–4635.

Hoffman, C. S., and F. Winston, 1987, A ten minute DNA preparation from yeast efficiently releases autonomous plasmids for transformations of Escherichia coli. Gene. 57:267–272.

Horn, N., S. Swindell, H. Dodd, and M. Gasson, 1991, Nisin biosynthesis genes are encoded by a novel conjugative transposon. Mol. Gen. Genet. 228:129–135.

Maniatis, T., E. F. Fritsch, and J. Sambrook, 1989, Molecular Cloning: A laboratory manual. Cold Spring Harbor Laboratory, Cold Spring Harbor, N.Y.

Mattick, A. T. R., and A. Hirsch, 1947, Further observations of an inhibitory substance (nisin) from lactic streptococci. Lancet 2:5–7.

Morris, S. L., R. C. Walsh, J. N. Hansen, 1984, Identification and characterisation of some bacterial membrane sulfhydryl groups which are targets of bacteriostatic and antibiotic action. J. Biol. Chem. 259:13590–13594.

Ogden K., and R. S. Tubb, 1985, Inhibition of beer-spoilage Lactic Acid Bacteria by nisin. J. Inst. Brew. 91:390–392.

Parente, E., and C. Hill, 1992, A comparison of factors affecting the production of two bacteriocins from lactic acid bacteria. J. Appl. Bacteriol. 73:290–298.

Piard, J. C., P. M. Muriana, M. J. Desmazeaud, and T. R. Klaenhammer, 1991, Purification and partial characterization of lacticin 481, a lanthionine-containing bacteriocin produced by Lactococcus lactis subsp. lactis CNRZ481. Appln. Environ. Microbiol. 58:279–284.

Rea, M. C., and T. M. Cogan, 1994, Buttermilk plants: the Irish version of Kefir. The Irish Scientist. 2:7.

Ruhr, E., and H. G. Sahl, 1985, Mode of action of the peptide antibiotic nisin and influence on the membrane potential of whole cells and on cytoplasmic and artificial membrane vesicles. Antimicrob. Agents Chemother. 27:841–845.

Steen, M. T., Y. J. Chung, and J. N. Hansen, 1994, Characterization of the nisin gene as part of a polycistronic operon in the chromosome of Lactococcus lactis ATCC11454. Appln. Environ. Microbiol. 57:1181–1188.

Stevens, K. A., B. W. Sheldon, N. A. Klapes, and T. R. Klaenhammer, 1992. Effect of treatment conditions on nisin inactivation of Gram negative bacteria. J. Food Prot. 55:763–766.

Swank, R. T. and K. D. Munkres, 1971, Molecular weight analysis of oligopeptides by electrophoresis in polyacrylamide gels with sodium dodecyl sulphate. Anal. Biochem. 39:462–477.

Marier & Boulet, J. Dairy Sci., 1958, 41, 1683.

Prill & Hammer, Iowa State Coll. J Sci., 1938, 12, 385.

Jordan & Cogan, Irish J. Agric. Food Res. 1995, 34, 39.

We claim:

1. An isolated naturally occurring bacteriocin designated lacticin 3147 from Lactococcus lactis DPC3147 characterised by a molecular weight of approximately 2.8 kDa, inhibiting activity against lactococci, lactobacilli, enterococci, bacilli, leuconostocs, pediococci, clostridia, staphylococci and streptococci sensitivity to the proteases trypsin, alpha-chymotrypsin, proteinase K and pronase E but not pepsin, heat-stability, activity at acid pH, and the capability of inhibiting nisin-producing bacterial strains.

2. *L. lactis* DPC3147 strain as deposited at the National Collection of Industrial and Marine Bacteria, Aberdeen, Scotland, on Apr. 11, 1995 under the Accession No. NCIMB 40716.

3. An isolated plasmid comprising gene(s) encoding a bacteriocin as defined in claim 1.

4. An isolated plasmid pMRC01 which comprises gene(s) which encode the bacteriocin designated lacticin 3147, lacticin 3147 immunity gene(s) and phage resistance genes as deposited at the National Collection of Industrial and Marine Bacteria, Aberdeen, Scotland, on Apr. 11, 1995 under Accession No. NCIMB 40716.

5. Isolated gene(s) which encode lacticin 3147 as deposited at the National Collection of Industrial and Marine Bacteria, Aberdeen, Scotland, on Apr. 11, 1995 under Accession No. NCIMB 40716.

6. An isolated gene encoding a protein or polypeptide conferring immunity to lacticin 3147 as deposited in the plasmid pMRCO1 as deposited at the National Collection of Industrial and Marine Bacteria, Aberdeen, Scotland, on Apr. 11, 1995 under Accession No. NCIMB 40716.

7. An isolated gene encoding a protein or polypeptide which confers resistance to a phage and as deposited at the National Collection of Industrial and Marine Bacteria, Aberdeen, Scotland, on Apr. 11, 1995 under the Accession No. NCIMB 40716.

8. A host cell into which a plasmid according to claim 3 or 4 has been introduced.

9. A method of producing lacticin 3147 comprising culturing a host cell as claimed in claim 2 containing lacticin 3147-encoding gene(s) and isolating lacticin 3147 from the culture.

10. A method of conferring lacticin 3147-producing properties on a host cell, comprising introducing and expressing in the host a plasmid as claimed in claim 3 or 4.

11. A food-grade genetic marker system comprising a gene for immunity to lacticin 3147 comprising a gene of claim 6.

12. A method of conferring phage resistance on a host cell, comprising introducing and expressing therein a gene as claimed in claim 7.

13. A food-grade genetic marker system comprising a gene for immunity to lacticin 3147 comprising a gene of claim 6.

14. The isolated bacteriocin-encoding gene of *L. lactis* strain DPC2949 as deposited at the National Collection of Industrial and marine Bacteria, Aberdeen, Scotland on Apr. 11, 1995 under the Accession No. NCIMB 40715.

15. An isolated bacteriocin produced by the *L. lactis* strain DPC2949 as claimed in claim 13.

16. A host cell comprising the gene as claimed in claim 14.

17. A method of preventing late gas-blowing in Cheddar cheese production comprising introducing into the starter culture a gene of claim 16.

18. A method of controlling non-starter lactic bacteria in Cheddar cheese production comprising introducing into the starter culture a gene of claim 14.

19. A host cell comprising gene(s) according to any of claims 5, 6 or 7.

20. A method for producing lacticin 3147 which comprises growing the host cell of claim 19 under conditions which favor the expression of lacticin 3147.

21. A host cell comprising of gene(s) according to any of claims 5, 6 or 7.

22. A method of inhibiting or preventing the growth of a microorganism comprising contacting a composition with an effective amount of the gene of claim 14 an culturing the composition under conditions for the expression of the gene.

23. A method of inhibiting or preventing the growth of a microorganism comprising contacting the microorganism with an effective amount of the bacteriocin of claim 1.

24. A method of treating bovine mastitis in an animal comprising administering to the animal an effective amount of the compound of claim 1, effective to treat mastitis.

25. A composition comprising the bacteriocin of claim 1.

26. A composition for the treatment of mastitis comprising an effective amount of the bacteriocin of claim 1 and a carrier.

27. A composition for oral hygiene comprising an effective amount of the bacteriocin of claim 1 and a carrier.

28. The composition of claim 27, wherein the carrier is an oral or dental product.

29. A composition comprising the gene of claim 14 and a carrier.

30. An isolated plasmid comprising gene(s) according to claim 5.

31. An isolated Lacticin 3147 as produced by the strain of claim 2.

32. An isolated Lacticin 3147 as encoded by the plasmid of claim 4.

33. An isolated plasmid comprising gene(s) according to claim 5.

34. An isolated Lacticin 3147 as encoded by the gene of claim 7.

35. An isolated Lacticin 3147 as produced by the cell of claim 8.

36. An isolated Lacticin 3147 as encoded by the gene(s) of claim 5.

* * * * *

UNITED STATES PATENT AND TRADEMARK OFFICE
CERTIFICATE OF CORRECTION

PATENT NO.   : 6,207,411 B1
DATED        : March 27, 2001
INVENTOR(S)  : Reynolds Paul Ross et al.

It is certified that error appears in the above-identified patent and that said Letters Patent is hereby corrected as shown below:

Column 25,
Lines 49-51, please replace "13. A food grade genetic marker system comprising a gene for immunity to lacticin 3147 comprising a gene of claim 6." with
-- 13. *L. lactis* strain DPC2949 as depositied at the National Collection of Industrial and marine Bacteria, Aberdeen, Scotland on Apr. 11, 1995 under Accession No. NCIMB40715. --;

Column 26,
Line 7, please replace "a gene of claim 16" with -- a gene of claim 14 --;
Lines 16-17, please replace "21. A host cell comprising of gene(s) according to any of claims 5, 6, or 7." with
-- 21. An isolated Laciticin 3147 produced according to the method of claim 20. --;
Line 21, please replace "claim 14 an culturing" with -- claim 14 and culturing --;
Lines 45 and 46, please replace "33. An isolated plasmid comprising gene(s) according to claim 5." with
-- 33. An isolated Laciticin 3147 as encoded by the gene of claim 5. --;
Lines 51 and 52, please replace "36. An isolated Lacticin 3147 as encoded by the gene(s) of claim 5." with
-- 36. An isolated Laciticin 3147 as encoded by the plasmid of claim 30. --.

Signed and Sealed this

Nineteenth Day of August, 2003

JAMES E. ROGAN
*Director of the United States Patent and Trademark Office*